US008748146B2

(12) United States Patent
Lippow et al.

(10) Patent No.: US 8,748,146 B2
(45) Date of Patent: Jun. 10, 2014

(54) ENGINEERED NUCLEASES AND THEIR USES FOR NUCLEIC ACID ASSEMBLY

(75) Inventors: Shaun Lippow, San Francisco, CA (US); Dasa Lipovsek, Cambridge, MA (US); Patricia M. Aha, Groton, MA (US)

(73) Assignee: Celexion, LLC, Cambridge, MA (US)

( * ) Notice: Subject to any disclaimer, the term of this patent is extended or adjusted under 35 U.S.C. 154(b) by 1148 days.

(21) Appl. No.: 12/596,546

(22) PCT Filed: Apr. 19, 2008

(86) PCT No.: PCT/US2008/005021
§ 371 (c)(1),
(2), (4) Date: Jan. 3, 2011

(87) PCT Pub. No.: WO2008/130629
PCT Pub. Date: Oct. 30, 2008

(65) Prior Publication Data
US 2011/0117625 A1    May 19, 2011

Related U.S. Application Data

(60) Provisional application No. 60/925,507, filed on Apr. 19, 2007.

(51) Int. Cl.
*C12N 9/10* (2006.01)
*C12N 9/12* (2006.01)

(52) U.S. Cl.
USPC .......... 435/193; 435/183; 435/199; 435/69.7; 530/350

(58) Field of Classification Search
None
See application file for complete search history.

(56) References Cited

U.S. PATENT DOCUMENTS

| | | | |
|---|---|---|---|
| 5,436,150 A | 7/1995 | Chandrasegaran | |
| 2005/0026157 A1 | 2/2005 | Baltimore | |
| 2005/0202498 A1 | 9/2005 | Kim | |
| 2005/0208489 A1 | 9/2005 | Carroll | |
| 2007/0042404 A1 | 2/2007 | Zhao | |

FOREIGN PATENT DOCUMENTS

WO    WO 00/46386    8/2000

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Arnould, Sylvain et al., Engineering of Large Numbers of Highly Specific Homing Endonucleases that Induce Recombination on Novel DNA Targets, *J. Mol. Biol.* vol. 355, No. 3, pp. 443-458 (Jan. 20, 2006).
Bath, Abigail J. et al., Many Type IIs Restriction Endonucleases Interact with Two Recognition Sites before Cleaving DNA, *J. Biol. Chem*, vol. 277, No. 6, pp. 4024-4033 (Feb. 8, 2002).
Beumer, Kelly et al., Efficient Gene Targeting in *Drosophila* With Zinc-Finger Nucleases, *Proc. Natl. Acad. Sci. USA*, vol. 105, No. 50, pp. 19821-19826 (Dec. 16, 2008).
Bibikova, Marina et al., Targeted Chromosomal Cleavage and Mutagenesis in *Drosophila* Using Zinc-Finger Nucleases, *Genetics*, vol. 161, No. 3, pp. 1169-1175 (Jul. 2002).
Bitinaite, Jurate et al., FokI Dimerization is Required for DNA Cleavage, *Proc. Natl. Acad. Sci. USA*, vol. 95 pp. 10570-10575 (Sep. 1998).
Carr, Peter A. et al., Protein-Mediated Error Correction for *De Novo* DNA Synthesis, *Nucleic Acids Research*, vol. 32, No. 20, pp. 1-9 (Nov. 23, 2004).
Cello, Jeronimo et al., Chemical Synthesis of Poliovirus cDNA: Generation of Infectious Virus in the Absence of Natural Template, *Science* , vol. 297, No. 5583, pp. 1016-1018 (Aug. 9, 2002).
Chan, Siu-hong et al., Catalytic Domain of Restriction Endonuclease BmrI as a Cleavage Module for Engineering Endonucleases with Novel Substrate Specificities, *Nucleic Acids Research*, vol. 35, o. 18, pp. 6238-6248 (Sep. 3, 2007).
Chen, Zhilei et al., A Highly Sensitive Selection Method for Directed Evolution of Homing Endonucleases, *Nucleic Acids Research*, vol. 33, No. 18, pp. 154-160 (Sep. 18, 2005).
Chen, Zhilei et al., Directed Evolution of Homing Endonuclease I-SceI with Altered Sequence Specificity, *Protein Engineering, Design & Selection*, vol. 22, No. 4. pp. 249-256 (Jan. 28, 2009).
Chevalier, Brett S., Homing Endonucleases: Structural and Functional Insight into the Catalysts of Intron/Intein Mobility, *Nucleic Acids Research*, vol. 29, No. 18, pp. 3757-3774 (Apr. 30, 2001).
Chevalier, B. S. et al., Design, activity, and structure of highly specific artificial endonuclease. Mol. Cell., 10, 895-905, 2002.
Clark, James M., Novel Non-Templated Nucleotide Addition Reactions Catalyzed by Procaryotic and Eucaryotic DNA Polymerases, *Nucleic Acids Research*, vol. 16, No. 20 (Sep. 12, 1988).
Colleaux, L., et al., Recognition and Cleavage Site of the Intron-Encoded Omega Transposase, *Proc. Natl. Acad. Sci. USA*, vol. 85, pp. 6022-6026 (Aug. 1988).
Cornu, Tatjana I. et al., DNA-Binding Specificity is a Major Determinant of the Activity and Toxicity of Zinc-Finger Nucleases, *Molecular Therapy*, vol. 16, No. 2, pp. 352-358 (Feb. 2008).
Derbyshire,V., et al. Two-domains Structure of the td Intron-encoded Endonuclease I-TevI correlates with the two-domain configuration of the Homing Site. (1997) J. Mol. Biol., 265, 494-506.
Doyon, Jeffrey B. et al., Directed Evolution and Substrate Specificity Profile of Homing Endonuclease I-SceI, *J. Am. Chem. Soc.*, vol. 128, pp. 2477-2484 (Jan. 31, 2006).
Durai, Sundar et al., Zinc Finger Nucleases: Custom-Designed Molecular Scissors for Genome Engineering of Plant and Mammalian Cells, *Nucleic Acids Research*, vol. 33, No. 18, pp. 5978-5990 (Oct. 26, 2005).
Epinat, Jean-Charles et al., A Novel Engineered Meganuclease Induces Homologous Recombination in Yeast and Mammalian Cells, *Nucleic Acids Research*, vol. 31, No. 11, pp. 2952-2962 (Mar. 31, 2003).

(Continued)

*Primary Examiner* — Richard Hutson
(74) *Attorney, Agent, or Firm* — Greenberg Traurig, LLP; Natalie Salem

(57) ABSTRACT

Aspects of the invention provide engineered endonucleases that are characterized by both a long recognition sequence and specific cleavage outside of the recognition site. Engineered endonucleases of the invention are useful for manipulating long pieces of DNA.

12 Claims, 9 Drawing Sheets

(56) References Cited

OTHER PUBLICATIONS

Flick, Karen E. et al., DNA Binding and Cleavage by the Nulear Intron-Encoded Homing Endonuclease I-*Ppo*I, *Nature*, vol. 394, pp. 96-101 (Jul. 2, 1998).
Forster, Anthony C. et al., Towards Synthesis of a Minimal Cell, *Molecular Systems Biology*, vol. 2, No. 45, pp. 1-10. (Jul. 26, 2006).
Gibson, Daniel G., et al. Complete Chemical Synthesis, Assembly, and Cloning of a Mycoplasma Genitalium Genome, *Science*, vol. 319, No. 5867, pp, 1215-1220 (Feb. 29, 2008).
Gruen, Mathias et al., An In Vivo Selection System for Homing Endonuclease Activity, *Nucleic Acids Research*, vol. 30, No. 7, pp. e29, 1-6 (Jan. 25, 2002).
Heath, P. J., et al.. (1997) "Structure of the I-CreI intron-encoded endonuclease: a novel fold that binds and cleaves a long DNA target sequence" Nature Structural Biology 4 (6): 468-476.
Huang B, et al., Splase: a new class IIS zinc-finger restriction endonuclease with specificity for Sp1 binding sites. J Protein Chem. 1996;15:481-489.
Ichiyanagi, K.; et al., Crystal structure of an archaeal intein-encoded homing endonuclease PI-PfuI. J Mol Biol 300(4): 889-901, 2000.
Jurenaite-Urbanaviciene, Sonata et al., Generation of DNA Cleavage Specificities of Type II Restriction Endonucleases by Reassortment of Target Recognition Domains, *PNAS*, vol. 104, No. 25, pp. 10358-10363 (Jun. 19, 2007).
Jurica, M. S. and Stoddard , Homing endonucleases: structure, function and evolution. Cell Mol. Life Sci. 55:1304-1326, 1999.
Kappelman, JR. et al. , SgfI, a new type-II restriction endonuclease that recognizes the octanucleotide sequence 5'-GCGAT/CGC-3', Gene. Jul. 4, 1995;160(1):55-8.
Kim, Yang-Gyun et al., Chimeric restriction enzyme: Gal4 fusion to FokI cleavage domain., Biol Chem. Apr.-May 1998; 379(4-5):489-95.
Kim, Yang-Gyun et al., Chimeric Restriction Endonuclease, *Proc. Natl. Acad. Sci. USA*, vol. 91, pp. 883-887 (Feb. 1994).
Kim, Yang-Gyun et al., Hybrid Restriction Enzymes: Zinc Finger Fusions to Fok I Cleavage Domain, *Proc. Natl. Acad. Sci. USA*, vol. 93, pp. 1156-1160 (Feb. 1996).
Kodumal, Sara J., et al., Total Synthesis of Long DNA Sequences: Synthesis of a Contiguous 32-kb Polyketide Synthase Gene Cluster, *PNAS*, vol. 101, No. 44, pp. 15573-15578 (Nov. 2, 2004).
Kotani H. et al., Sse8387I, a new type-II restriction endonuclease that recognizes the octanucleotide sequence 5'-CCTGCAGG-3'., Nucleic Acids Res. Oct. 11, 1990; 18(19): 5637-5640.
Lechner M.et al. , SwaI, a unique restriction endonuclease from *Staphylococcus warneri*, which recognizes 5'-ATTTAAAT-3', Nucleic Acids Res. May 11, 1992; 20(9): 2293-2296.
Li L. et al. , Alteration of the cleavage distance of Fok I restriction endonuclease by insertion mutagenesis., Proc Natl Acad Sci U S A. Apr. 1, 1993; 90(7): 2764-2768.
Li L, et al. , C-terminal Deletion Mutants of the FokI restriction Endonuclease. Gene. 1993; vol. 133:79-84.
Lippow, Shaun M., et al., Creation of a Type IIS Restriction Endonuclease with a Long Recognition Sequence, *Nucleic Acids Research*, vol. 37, No. 9, pp. 3061-3073 (Mar. 20, 2009).
Liu, Qiang, et al., Design of Polydactil Zinc-Finger Proteins for Unique Addressing Within Complex Genomes, *Proc. Natl. Acad. Sci. USA*, vol. 94, pp. 5525-5530 (May 1997).
Maeder, Morgan L., et al., Rapid "Open-Source" Engineering of Customized Zinc-Finger Nucleases for Highly Efficient Gene Modification, *Molecular Cell*, vol. 31, pp. 294-301 (Jul. 25, 2008).
Mandell, Jeffrey G., Zinc Finger Tools: Custom DNA-Binding Domains for Transcription Factors and Nucleases, *Nucleic Acids Research*, vol. 34, W516-W523 (Mar. 24, 2006).
Moehle, Erica A., et al., Targeted Gene Addition into a Specified Location in the Human Genome Using Designed Zinc Finger Nucleases, *PNAS*, vol. 104, No. 9, pp. 3055-3060 (Feb. 27, 2007).
Monteilhet C. et al.., Purification and characterization of the in vitro activity of I-Sce I, a novel and highly specific endonuclease encoded by a group I intron , Nuclic Acids Research vol. 18, No, 6, 1407-1413, 1990.

Morton, Jason et al., Induction and Repair of Zinc-Finger Nuclease-Targeted Double-Strand Breaks in *Caenorhabditis elegans* Somatic Cells, *PNAS*, vol. 103, No. 44, pp. 16370-16375 (Oct. 31, 2006).
Moure, C. M., Gimble, F. S., & Quiocho, F. A. (2003). The crystal structure of the gene targeting homing endonuclease I-SceI reveals the origins of its target site specificity. J. Mol. Biol., 334, 685-695.
Nelson, Janise Meyertons, et al., FseI, a New Type II Restriction Endonuclease That Recognizes the Octanucleotide Sequence 5' GGCCGGCC 3', *Nucleic Acids Research*, vol. 18, No. 8, pp. 2061-2064 (Feb. 26, 1990).
Newman M Structure of BamHI Endocnuclease bound to DNA: partial folding and unfolding of DNA binding , Science 1995, 269, 656-663, 1995.
Porteus, Matthew H., et al., Chimeric Nucleases Stimulate Gene Targeting in Human Cells, *Science*, vol. 300, p. 763 (May 2, 2003).
Porteus, Matthew H., et al., Gene Targeting Using Zinc Finger Nucleases, *Nature Biotechnology*, vol. 23, No. 8, pp. 967-973 (Aug. 2005).
Qiang, Bo-Qin, et al., A Type II Restriction Endonuclease with an Eight Nucleotide Specificity from *Streptomyces Fimbriatus*, *Nucleic Acids Research*, vol. 12, No. 11, pp. 4507-4516 (May 8, 1984).
Qiang, Bo-Qin, et al., Two Unique Restriction Endonucleases from *Neisseria iactamica*, *Nucleic Acids Research*, vol. 14, No. 5, pp. 1991-1999 (Feb. 5, 1986).
Qiang BP Schildkraut I, Not I and SfiI : restriction enzyme with octanucleotide recognition sequences Methods Enzymol. 155: 15-21, 1987.
Roberts, Richard J., et al., REBASE—Restriction Enzymes and DNA Methyltransferases, *Nucleic Acids Research*, vol. 33, Database Issue, pp. D230-D232 (Jan. 1, 2005).
Rosen, Laura E., et al., Homing Endonuclease I-CreI Derivatives with Novel DNA Target Specificities, *Nucleic Acids Research*, vol. 34, No. 17, pp. 4791-4800 (Sep. 13, 2006).
Scalley-Kim, Michelle, et al., Coevolution of a Homing Endonuclease and Its Host Target Sequence, *J. Mol. Biol.*, vol. 372, No. 5, pp. 1305-1319 (Oct. 5, 2007).
Seligman, Lenny M., et al., Mutations Altering the Cleavage Specificity of a Homing Endonuclease, *Nucleic Acids Research*, vol. 30, No. 17, pp. 3870-3879 (Jul. 8, 2002).
Shevchuk, Nikolai A., et al., Constructino of Long DNA Molecules Using Long PCR-Based Fusion of Several Fragments Simultaneously, *Nucleic Acids Research*, vol. 32, No. 2, pp. 1-12, Jan. 2004.
Smith, Hamilton O., et al. Generating a Synthetic Genome by Whole Genome Assembly: ØX174 Bacteriophage from Synthetic Oligonucleotides, *PNAS*, vol. 100, No. 26, pp. 15440-15445 (Dec. 23, 2003).
Smith, Jeff, et al., Requirements for Double-Strand Cleavage by Chimeric Restriction Enzymes with Zinc Finger DNA-Recognition Domains, *Nucleic Acids Research*, vol. 28, No. 17, pp. 3361-3369 (Jul. 3, 2000).
Smith, Julianne, et al., A Combinatorial Approach to Create Artificial Homing Endonucleases Cleaving Chosen Sequences, *Nucleic Acids Research*, vol. 34, No. 22, pp. 1-12 (Nov. 27, 2006.
Sussman, Django, et al., Isolation and Characterization of New Homing Endonuclease Specificities at Individual Target Site Positions, *J.Mol. Biol.*, vol. 342, pp. 31-41 (Jul. 31, 2004).
Thierry, Agnes, et al., Cleavage of Yeast and Bacteriophage T7 Genomes at a Single Site Using the Rare Cutter Endonuclease I-*SCE* I, *Nucleic Acids Research*, vol. 19, No. 1, pp. 189-190 (Jan. 11, 1991).
Umov, Fyodor D., et al., Highly Efficient Endogenous Human Gene Correction Using Designed Zinc-Finger Nucleases, *Nature*, vol. 435, No. 2, pp. 646-651 (Jun. 2, 2005).
Van Roey, Patrick, et al., Intertwined Structore of the DNA-Binding Domain of Intron Endonuclease I-*Tev*I With its Substrate, *The EMBO Journal*, vol. 20, No. 14, pp. 331-3637, (Jul. 17, 2000).
Vanamee, Eva Scheuring, et al., An EM View of the Fok1 Synaptic Complex by Single Particle Analysis, *J. Mol. Biol.*, vol. 370, No. 2, pp. 207-212 (Jul. 6, 2007).
Volna, Petra et al., Flow Cytometric Analysis of DNA Binding and Cleavage by Cell Surface-Displayed Homing Endonucleases, *Nucleic Acids Research*, vol. 35, No. 8, pp. 248-2758 (Apr. 10, 2007).
Wah, David A., et al., Structure of the Multimodular Endonuclease Fok1 Bound to DNA, *Nature*, vol. 388, pp. 97-100 (Jul. 3, 1997).

(56) References Cited

OTHER PUBLICATIONS

Wah, David A., et al., Structure of *Fok*1 Has Implications for DNA Cleavage, *Proc. Natl. Acad. Sci. USA*, vol. 95, pp. 10564-10569 (Sep. 1998).

Waugh, David S., et al., A Novel Class of *Fok*1 Restriction Endonuclease Mutants That Cleave Hemi-methylated Substrates, *Journal of Biological Chemistry*, vol. 269, No. 16, pp. 12298-12303 (Apr. 22, 1994).

Williams R.W. et al., Secondary Structure Predictions and Medium Range Interactions, Biochim Biophys Acta 916: 200-204, 1987.

Wilmot C.M. et al., Analysis and prediction of the different types of beta-turn in proteins., 1988, J. Mol. Biol. 203:221-232.

Xu, Lin, et al., Average Gene Length Is Highly Conserved in Prokaryotes and Eukaryotes and Diverges Only Between the Two Kingdoms, *Mol. Biol. Evol.* vol. 23, No. 6, pp. 1107-1108 (Apr. 12, 2006).

Yount, Boyd, et al., Strategy for Systematic Assembly of Large RNA and DNA Genomes: Transmissible Gastroenteritis Virus Model, *Journal of Virology*, vol. 74, No. 22, pp. 10600-10611 (Aug. 15, 2000).

Zhang, Penghua, et al., Rational Design of a Chimeric Endonuclease Targeted to Not1 Recognition Site, *Protein Eng. Des. Sel.*, vol. 20, No. 10, pp. 497-504 (Oct. 2007).

Zhou, Huan-Xiang, Polymer Models of Protein Stability, Folding, and Interactions, *Biochemistry*, vol. 43, No. 8, pp. 2141-2154 (Mar. 2, 2004).

H.-X. Zhou . Quantitative account of the enhanced affinity of two linked scFvs specific for different epitopes on the same antigen. J. Mol. Biol. 329, 1-8, (2003).

Steuer, Shawn et al., Chimeras of the Homing Endonuclease PI-SceI and the Homologous *Candida tropicalis* Intein: A Study to Explore the Possibility of Exchanging DNA-Binding Modules to Obtain Highly Specific Endonucleases with Altered Specificity, *Chembiochem*, vol. 5, No. 2, pp. 206-213 (2004).

International Search Report based on PCT/US2008/005021 dated Nov. 3, 2009.

I-SceI ,New England Biolabs, Certificate of Analysis.

* cited by examiner

SEQUENCE LISTING

<160> NUMBER OF SEQ ID NOS: 53

<210> SEQ ID NO 1
<211> LENGTH: 18
<212> TYPE: DNA
<213> ORGANISM: Artificial Sequence
<220> FEATURE:
<223> OTHER INFORMATION: oligonucleotide

<400> SEQUENCE: 1
tagggataac agggtaat                                          18

<210> SEQ ID NO 2
<211> LENGTH: 18
<212> TYPE: DNA
<213> ORGANISM: Artificial Sequence

```
<220> FEATURE:
<223> OTHER INFORMATION: oligonucleotide

<400> SEQUENCE: 2
attaccctgt tatccta                                                     18

<210> SEQ ID NO 3
<211> LENGTH: 33
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (19)..(33)
<223> OTHER INFORMATION: n is a, c, g or t

<400> SEQUENCE: 3
tagggataac agggtaatnn nnnnnnnnn nnn                                    33

<210> SEQ ID NO 4
<211> LENGTH: 33
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(15)
<223> OTHER INFORMATION: n is a, c, g or t

<400> SEQUENCE: 4
nnnnnnnnnn nnnnnattac cctgttatcc cta                                   33

<210> SEQ ID NO 5
<211> LENGTH: 20
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (6)..(20)
<223> OTHER INFORMATION: n is a, c, g or t

<400> SEQUENCE: 5
ggatgnnnnn nnnnnnnnnn                                                  20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(15)
<223> OTHER INFORMATION: n is a, c, g or t

<400> SEQUENCE: 6
nnnnnnnnnn nnnnncatcc                                                  20

<210> SEQ ID NO 7
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
```

```
<222> LOCATION: (1)..(4)
<223> OTHER INFORMATION: n is a, c, g or t
<220> FEATURE:
<221> NAME/KEY: misc_feature
<222> LOCATION: (23)..(26)
<223> OTHER INFORMATION: n is a, c, g or t

<400> SEQUENCE: 7
nnnnattacc ctgttatccc tannnn                                         26

<210> SEQ ID NO 8
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (23)..(26)
<223> OTHER INFORMATION: n is a, c, g or t

<400> SEQUENCE: 8
nnnntaggga taacagggta atnnnn                                         26

<210> SEQ ID NO 9
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(4)
<223> OTHER INFORMATION: n is a, c, g or t
<220> FEATURE:
<221> NAME/KEY: misc_feature
<222> LOCATION: (10)..(26)
<223> OTHER INFORMATION: n is a, c, g or t

<400> SEQUENCE: 9
nnnnggatgn nnnnnnnnn nnnnnn                                          26

<210> SEQ ID NO 10
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(17)
<223> OTHER INFORMATION: n is a, c, g or t
<220> FEATURE:
<221> NAME/KEY: misc_feature
<222> LOCATION: (23)..(26)
<223> OTHER INFORMATION: n is a, c, g or t

<400> SEQUENCE: 10
nnnnnnnnnn nnnnnnncat ccnnnn                                         26

<210> SEQ ID NO 11
<211> LENGTH: 31
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
```

```
<222> LOCATION: (1)..(4)
<223> OTHER INFORMATION: n is a, c, g or t
<220> FEATURE:
<221> NAME/KEY: misc_feature
<222> LOCATION: (23)..(31)
<223> OTHER INFORMATION: n is a, c, g or t

<400> SEQUENCE: 11
nnnnattacc ctgttatccc tannnnnnnn n                              31

<210> SEQ ID NO 12
<211> LENGTH: 31
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)..(9)
<223> OTHER INFORMATION: n is a, c, g or t
<220> FEATURE:
<221> NAME/KEY: misc_feature
<222> LOCATION: (28)..(31)
<223> OTHER INFORMATION: n is a, c, g or t

<400> SEQUENCE: 12
nnnnnnnnnt agggataaca gggtaatnnn n                              31

<210> SEQ ID NO 13
<211> LENGTH: 31
<212> TYPE: DNA
<213> ORGANISM: Artificial Sequence
<220> FEATURE:
<223> OTHER INFORMATION: oligonucleotide

<400> SEQUENCE: 13
agtttggatt catatattat taccctgtta t                              31

<210> SEQ ID NO 14
<211> LENGTH: 27
<212> TYPE: DNA
<213> ORGANISM: Artificial Sequence
<220> FEATURE:
<223> OTHER INFORMATION: oligonucleotide

<400> SEQUENCE: 14
cagggtaata atatatgcct ccaaact                                   27

<210> SEQ ID NO 15
<211> LENGTH: 23
<212> TYPE: DNA
<213> ORGANISM: Artificial Sequence
<220> FEATURE:
<223> OTHER INFORMATION: oligonucleotide

<400> SEQUENCE: 15
ccctagcgtg caggacaggc ttc                                       23

<210> SEQ ID NO 16
<211> LENGTH: 27
<212> TYPE: DNA
<213> ORGANISM: Artificial Sequence
<220> FEATURE:
<223> OTHER INFORMATION: oligonucleotide

<400> SEQUENCE: 16
gaagcctgtc ctgcacgcta gggataa                                   27
```

```
<210> SEQ ID NO 17
<211> LENGTH: 24
<212> TYPE: DNA
<213> ORGANISM: Artificial Sequence
<220> FEATURE:
<223> OTHER INFORMATION: oligonucleotide

<400> SEQUENCE: 17
tattattacc ctgttatccc tagc                                          24

<210> SEQ ID NO 18
<211> LENGTH: 29
<212> TYPE: DNA
<213> ORGANISM: Artificial Sequence
<220> FEATURE:
<223> OTHER INFORMATION: oligonucleotide

<400> SEQUENCE: 18
tgcacgctag ggataacagg gtaataata                                     29

<210> SEQ ID NO 19
<211> LENGTH: 23
<212> TYPE: DNA
<213> ORGANISM: Artificial Sequence
<220> FEATURE:
<223> OTHER INFORMATION: oligonucleotide

<400> SEQUENCE: 19
gtgcaggaca ggcttcggaa cca                                           23

<210> SEQ ID NO 20
<211> LENGTH: 18
<212> TYPE: DNA
<213> ORGANISM: Artificial Sequence
<220> FEATURE:
<223> OTHER INFORMATION: oligonucleotide

<400> SEQUENCE: 20
tggttccgaa gcctgtcc                                                 18

<210> SEQ ID NO 21
<211> LENGTH: 23
<212> TYPE: DNA
<213> ORGANISM: Artificial Sequence
<220> FEATURE:
<223> OTHER INFORMATION: oligonucleotide

<400> SEQUENCE: 21
tattattacc ctgttatccc tag                                           23

<210> SEQ ID NO 22
<211> LENGTH: 27
<212> TYPE: DNA
<213> ORGANISM: Artificial Sequence
<220> FEATURE:
<223> OTHER INFORMATION: oligonucleotide

<400> SEQUENCE: 22
cacgctaggg ataacagggt aataata                                       27

<210> SEQ ID NO 23
<211> LENGTH: 24
<212> TYPE: DNA
<213> ORGANISM: Artificial Sequence
<220> FEATURE:
<223> OTHER INFORMATION: oligonucleotide

<400> SEQUENCE: 23
```

```
cgtgcaggac aggcttcgga acca                                    24

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
tggttccgaa gcctgtcctg                                         20

<210> SEQ ID NO 25
<211> LENGTH: 30
<212> TYPE: DNA
<213> ORGANISM: Artificial Sequence
<220> FEATURE:
<223> OTHER INFORMATION: oligonucleotide

<400> SEQUENCE: 25
ctgggttcaa aacgtcgtga gacagtttgg                              30

<210> SEQ ID NO 26
<211> LENGTH: 30
<212> TYPE: DNA
<213> ORGANISM: Artificial Sequence
<220> FEATURE:
<223> OTHER INFORMATION: oligonucleotide

<400> SEQUENCE: 26
agttacgcta gggataacag ggtaatatag                              30

<210> SEQ ID NO 27
<211> LENGTH: 25
<212> TYPE: PRT
<213> ORGANISM: Artificial Sequence
<220> FEATURE:
<223> OTHER INFORMATION: synthesized

<400> SEQUENCE: 27

Gly Gly Ser Gly Gly Gly Ser Gly Asp Gly Ser Gly Asn Gly Gly Ser
1               5                   10                  15

Gly Gly Asp Ser Gly Gly Ser Gly Gly
            20                  25

<210> SEQ ID NO 28
<211> LENGTH: 25
<212> TYPE: PRT
<213> ORGANISM: Artificial Sequence
<220> FEATURE:
<223> OTHER INFORMATION: synthesized

<400> SEQUENCE: 28

Gly Gly Ser Gly Asp Arg Asp Gly Ser Asp Ser Asp Arg Pro Asp Ser
1               5                   10                  15

Asp Lys Asn Asp Asp Gly Ser Gly Gly
            20                  25

<210> SEQ ID NO 29
<211> LENGTH: 40
<212> TYPE: PRT
<213> ORGANISM: Artificial Sequence
<220> FEATURE:
<223> OTHER INFORMATION: synthesized

<400> SEQUENCE: 29
```

```
Gly Gly Ser Gly Gly Ser Gly Asn Gly Gly Ser Gly Gly Asp
1               5                   10                  15

Gly Ser Gly Arg Ser Gly Asn Gly Gly Gly Asp Gly Gly Ser
                20                  25                  30

Gly Gly Gly Ser Gly Ser Gly Gly
        35                  40
```

<210> SEQ ID NO 30
<211> LENGTH: 40
<212> TYPE: PRT
<213> ORGANISM: Artificial Sequence
<220> FEATURE:
<223> OTHER INFORMATION: synthesized

<400> SEQUENCE: 30

```
Gly Gly Ser Gly Gly Asp Ser Lys Asp Ser Asp Pro Arg Asp
1               5                   10                  15

Gly Asp Asn Ser Gly Gly Arg Asp Asn Pro Asp Ser Gly Ser Gly
                20                  25                  30

Ser Lys Asp Asp Gly Ser Gly Gly
        35                  40
```

<210> SEQ ID NO 31
<211> LENGTH: 75
<212> TYPE: PRT
<213> ORGANISM: Artificial Sequence
<220> FEATURE:
<223> OTHER INFORMATION: synthesized

<400> SEQUENCE: 31

```
Gly Gly Ser Gly Gly Asp Ser Gly Pro Ser Gly Gly Asn Gly Gly
1               5                   10                  15

Ser Gly Arg Asp Gly Gly Gly Ser Asn Gly Gly Ser Arg Gly Ser Gly
                20                  25                  30

Gly Asp Ser Gly Pro Ser Gly Gly Gly Asn Gly Gly Ser Gly Gly Ser
        35                  40                  45

Gly Lys Asp Gly Gly Gly Asn Gly Gly Ser Gly Gly Lys Asp Ser Gly
        50                  55                  60

Gly Asn Gly Gly Ser Gly Gly Gly Ser Gly Gly
65                  70                  75
```

<210> SEQ ID NO 32
<211> LENGTH: 75
<212> TYPE: PRT
<213> ORGANISM: Artificial Sequence
<220> FEATURE:
<223> OTHER INFORMATION: synthesized

<400> SEQUENCE: 32

```
Gly Ser Ser Gly Asp Gly Asp Ser Lys Asp Gly Ser Asp Pro Asp Asn
1               5                   10                  15

Gly Asp Ser Arg Asp Gly Gly Asn Pro Gly Asp Gly Ser Gly Arg Asp
                20                  25                  30

Gly Asp Gly Ser Gly Asp Asn Gly Asp Gly Pro Ser Arg Ser Asp Ser
        35                  40                  45

Lys Ser Ser Asp Asp Ser Asp Lys Asn Pro Asp Gly Asp Ser Gly Asp
        50                  55                  60

Arg Ser Asp Gly Asp Lys Asp Gly Ser Gly Gly
65                  70                  75
```

```
<210> SEQ ID NO 33
<211> LENGTH: 15
<212> TYPE: PRT
<213> ORGANISM: Artificial Sequence
<220> FEATURE:
<223> OTHER INFORMATION: synthesized

<400> SEQUENCE: 33

Gln Phe Val Ile Pro Asn Arg Gly Val Thr Lys Gln Leu Val Lys
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: synthesized

<400> SEQUENCE: 34

Gln Phe Val Ile Pro Asn Arg Gly Val Thr Lys Gln Leu Phe Val Lys
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: synthesized

<400> SEQUENCE: 35

Gly Gly Ser Gly Gly Asp Gly Ser Gly Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: synthesized

<400> SEQUENCE: 36

Gly Gly Asp Ser Arg Asp Ser Asp Gly Gly
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthesized

<400> SEQUENCE: 37

Gly Gly Ser Gly Gly Ser Gly Asp Gly Gly Ser Gly Gly
1               5                   10

<210> SEQ ID NO 38
<211> LENGTH: 14
<212> TYPE: PRT
<213> ORGANISM: Artificial Sequence
<220> FEATURE:
<223> OTHER INFORMATION: synthesized

<400> SEQUENCE: 38

Gly Gly Asp Ser Arg Asp Pro Ser Asp Lys Ser Asp Gly Gly
1               5                   10

<210> SEQ ID NO 39
<211> LENGTH: 20
```

```
<212> TYPE: PRT
<213> ORGANISM: Artificial Sequence
<220> FEATURE:
<223> OTHER INFORMATION: synthesized

<400> SEQUENCE: 39

Gly Gly Gly Ser Gly Gly Ser Asp Gly Ser Gly Asn Gly Gly Ser Gly
1               5                   10                  15

Ser Gly Gly Gly
            20

<210> SEQ ID NO 40
<211> LENGTH: 20
<212> TYPE: PRT
<213> ORGANISM: Artificial Sequence
<220> FEATURE:
<223> OTHER INFORMATION: synthesized

<400> SEQUENCE: 40

Gly Gly Ser Gly Asp Arg Asp Asp Ser Asp Pro Ser Asp Lys Asn Asp
1               5                   10                  15

Gly Ser Gly Gly
            20

<210> SEQ ID NO 41
<211> LENGTH: 22
<212> TYPE: PRT
<213> ORGANISM: Artificial Sequence
<220> FEATURE:
<223> OTHER INFORMATION: synthesized

<400> SEQUENCE: 41

Gly Gly Gly Ser Gly Gly Ser Gly Asp Gly Ser Gly Asn Gly Gly Ser
1               5                   10                  15

Ser Gly Ser Gly Gly Gly
            20

<210> SEQ ID NO 42
<211> LENGTH: 22
<212> TYPE: PRT
<213> ORGANISM: Artificial Sequence
<220> FEATURE:
<223> OTHER INFORMATION: synthesized

<400> SEQUENCE: 42

Gly Gly Ser Gly Asp Arg Asp Gly Asp Ser Asp Pro Ser Asp Lys Asn
1               5                   10                  15

Asp Asp Gly Ser Gly Gly
            20

<210> SEQ ID NO 43
<211> LENGTH: 30
<212> TYPE: PRT
<213> ORGANISM: Artificial Sequence
<220> FEATURE:
<223> OTHER INFORMATION: synthesized

<400> SEQUENCE: 43

Gly Gly Ser Gly Gly Gly Ser Gly Asp Gly Ser Gly Gly Gly Ser
1               5                   10                  15

Gly Gly Asn Ser Gly Gly Asp Gly Ser Gly Gly Ser Gly Gly
                20                  25                  30

<210> SEQ ID NO 44
<211> LENGTH: 30
```

```
<212> TYPE: PRT
<213> ORGANISM: Artificial Sequence
<220> FEATURE:
<223> OTHER INFORMATION: synthesized

<400> SEQUENCE: 44

Gly Gly Ser Gly Asp Gly Arg Asp Gly Ser Asp Asn Ser Gly Asp Asp
1               5                   10                  15

Arg Pro Asp Ser Gly Asp Lys Asn Asp Asp Gly Ser Gly Gly
            20                  25                  30

<210> SEQ ID NO 45
<211> LENGTH: 18
<212> TYPE: PRT
<213> ORGANISM: Artificial Sequence
<220> FEATURE:
<223> OTHER INFORMATION: synthesized

<400> SEQUENCE: 45

Met Gly His His His His His His Glu Asn Leu Tyr Phe Gln Gly Ser
1               5                   10                  15

Gly Ser

<210> SEQ ID NO 46
<211> LENGTH: 142
<212> TYPE: DNA
<213> ORGANISM: Artificial Sequence
<220> FEATURE:
<223> OTHER INFORMATION: oligonucleotide

<400> SEQUENCE: 46
aattctggtt ccgaagcctg tcctgcacgc tagggataac agggtaataa tatatgaatc     60
caaactagag cggggctctt gacgtttggc tcaaaacgtc gtgagacagt ttggtcagtt    120
gtaaatatct aatattccaa tg                                              142

<210> SEQ ID NO 47
<211> LENGTH: 142
<212> TYPE: DNA
<213> ORGANISM: Artificial Sequence
<220> FEATURE:
<223> OTHER INFORMATION: oligonucleotide

<400> SEQUENCE: 47
gatccattgg aatattagat atttacaact gaccaaactg tctcacgacg ttttgagcca     60
aacgtcaaga gccccgctct agtttggatt catatattat taccctgtta tccctagcgt    120
gcaggacagg cttcggaacc ag                                              142

<210> SEQ ID NO 48
<211> LENGTH: 80
<212> TYPE: DNA
<213> ORGANISM: Artificial Sequence
<220> FEATURE:
<223> OTHER INFORMATION: oligonucleotide

<400> SEQUENCE: 48
gaattctggt tccgaagcct gtcctgcacg ctagggataa cagggtaata atatatgaat     60
ccaaactaga gcggggctct                                                 80

<210> SEQ ID NO 49
<211> LENGTH: 80
<212> TYPE: DNA
<213> ORGANISM: Artificial Sequence
<220> FEATURE:
```

```
<223> OTHER INFORMATION: oligonucleotide

<400> SEQUENCE: 49
agagccccgc tctagtttgg attcatatat tattaccctg ttatccctag cgtgcaggac      60
aggcttcgga accagaattc                                                 80

<210> SEQ ID NO 50
<211> LENGTH: 20
<212> TYPE: DNA
<213> ORGANISM: Artificial Sequence
<220> FEATURE:
<223> OTHER INFORMATION: oligonucleotide

<400> SEQUENCE: 50
attcgccatt caggctgcgc                                                 20

<210> SEQ ID NO 51
<211> LENGTH: 20
<212> TYPE: DNA
<213> ORGANISM: Artificial Sequence
<220> FEATURE:
<223> OTHER INFORMATION: oligonucleotide

<400> SEQUENCE: 51
cactttatgc ttccggctcg                                                 20

<210> SEQ ID NO 52
<211> LENGTH: 71
<212> TYPE: DNA
<213> ORGANISM: Artificial Sequence
<220> FEATURE:
<223> OTHER INFORMATION: oligonucleotide

<400> SEQUENCE: 52
ttcatgagac gatctccttc ctcttgatgg ctgtaataat agctctaggg cgatgttaag      60
acaacggatt c                                                          71

<210> SEQ ID NO 53
<211> LENGTH: 71
<212> TYPE: DNA
<213> ORGANISM: Artificial Sequence
<220> FEATURE:
<223> OTHER INFORMATION: oligonucleotide

<400> SEQUENCE: 53
ttcaatatat tattaccctg ttatccctag cgtgcaggac aggcttcgga accggagacg      60
ttgacaacat g                                                          71
```

ENGINEERED NUCLEASES AND THEIR USES FOR NUCLEIC ACID ASSEMBLY

This application is a national stage application of International Application No. PCT/US2008/005021 filed Apr. 19, 2008, which claims the benefit under 35 U.S.C. §119(e) from U.S. provisional application Ser. No. 60/925,507 entitled "Engineered nucleases and their uses for nucleic acid assembly" filed Apr. 19, 2007, now expired, the entire contents of both of which applications are herein incorporated by reference.

FIELD OF THE INVENTION

The invention relates to modified nucleases and uses thereof. In particular, the invention relates to modified sequence specific restriction endonucleases and uses thereof.

BACKGROUND

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Recombinant and synthetic nucleic acids also can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. Recombinant and synthetic nucleic acids also may be used as therapeutic compositions (e.g., for modifying gene expression, for gene therapy, etc.) or as diagnostic tools (e.g., as probes for disease conditions, etc.).

Numerous techniques have been developed for modifying existing nucleic acids (e.g., naturally occurring nucleic acids) to generate recombinant nucleic acids. For example, combinations of nucleic acid amplification, mutagenesis, nuclease digestion, ligation, cloning and other techniques may be used to produce many different recombinant nucleic acids. Chemically synthesized polynucleotides are often used as primers or adaptors for nucleic acid amplification, mutagenesis, and cloning.

Techniques also are being developed for de novo nucleic acid assembly whereby nucleic acids are made (e.g., chemically synthesized) and assembled to produce longer target nucleic acids of interest. For example, different multiplex assembly techniques are being developed for assembling oligonucleotides into larger synthetic nucleic acids that can be used in research, industry, agriculture, and/or medicine.

Many natural or engineered sequence specific endonucleases have been developed for manipulating nucleic acids (e.g., for cutting and assembling nucleic acids). However, additional engineered nucleases are useful as described herein.

SUMMARY OF THE INVENTION

Aspects of the invention relate to compositions and methods for cleaving nucleic acids at predetermined positions regardless of the nucleic acid sequences at the cleavage sites. In particular, aspects of the invention relate to engineered nucleases that can target a nucleic acid cleavage reaction to a unique position on a substrate nucleic acid regardless of the nucleic acid sequence at the position being cleaved. Methods of the invention can be used to cleave nucleic acid substrates and generate nucleic acid fragments having cleaved termini at predetermined positions within any sequence of interest. Aspects of the invention can be used to target a cleavage reaction to a unique position within a long nucleic acid substrate (e.g., 5 kb, 10 kb, 20 kb, 50 kb, 100 kb, 1 mb or longer). Aspects of the invention can increase the efficiency and accuracy of nucleic acid assembly procedures that involve one or more nucleic acid fragment assembly steps.

In one aspect, the invention relates to an engineered nuclease having i) a nucleic acid binding domain that recognizes and binds to a recognition sequence motif and ii) a nucleic acid cleavage domain that is not sequence specific. However, the binding and cleavage domains may be configured to cleave a target nucleic acid at a specific position outside of the nucleic acid motif recognized by the binding domain. The specific location of the cleavage site on a target nucleic acid may be determined by the relative positions of the binding and cleavage domains in the folded nuclease structure. The relative positions of these domains may be altered using an appropriate linker (e.g., a polypeptide linker) that connects the binding and cleavage domains.

Aspects of the invention relate to obtaining and/or modifying a nucleic acid binding domain from a first endonuclease (e.g., a natural endonuclease) and using it to target a chimeric endonuclease to a specific target sequence (e.g., one recognized by the natural endonuclease). In some embodiments, the endonuclease nucleic acid binding domain is modified to remove any associated nuclease activity. The nucleic acid binding domain is then connected to a nucleic acid cleavage domain from a second endonuclease to create a new chimeric enzyme.

According to aspects of the invention, by using a nucleic acid binding domain from an endonuclease, the chimeric endonuclease retains very tight binding and cleavage properties. Unlike chimeric endonucleases that use synthetic Zn fingers for binding, enzymes of the invention cut at a unique cleavage site relative to a binding site as opposed to exhibiting cleavage activity at two or more positions in a target nucleic acid relative to a binding site. Accordingly, aspects of the invention may be used to cleave at a unique specific position relative to the nucleic acid binding motif (as opposed to cutting at two or more positions relative to the binding motif). Accordingly, compositions and methods of the invention may be used to precisely cut a target nucleic acid and obtain homogeneous cleavage products that have a unique cleavage site (as opposed to a mixture of cleavage products that were cleaved at one of several positions). It should be appreciated however, that the cleavage site may result in a blunt end, a 3' overhang, or a 5' overhang, depending on the cleavage domain that is used.

In some embodiments, a nuclease is engineered to have a binding domain that binds to a long recognition motif that is present only rarely in a random nucleic acid sequence. These nucleases may be used to process and manipulate long nucleic acids without cleaving them at unwanted positions. A recognition sequence motif may be 8, 9, 10, 11, 12, 13, 14, 15, 16, 17, 18, 19, 20, 21, 22, 23, 24, 25, 26, 27, 28, 29, or 30 nucleotides long or longer (e.g., between 30 and 40, between 40 and 50, between 50 and 60, or more nucleotides long). The recognition motif may be single stranded or double-stranded.

The recognition motif may contain repeated or palindromic sequences or other sequence features as the invention is not limited in this respect.

In some embodiments, an engineered nuclease can be used to cleave a nucleic acid at any position and generate a fragment of interest having any desired sequence by providing a nucleic acid substrate that includes the fragment of interest appropriately configured adjacent to one or more contiguous flanking nucleic acid regions bearing a sequence motif recognized by a binding domain of the engineered nuclease. Cleavage by the nuclease releases the fragment of interest and separates it from the flanking region(s) containing the recognition motif(s).

In some embodiments, engineered nucleases can be used to process nucleic acid substrates to generate specific nucleic acid fragments for assembly into larger predetermined nucleic acid products. The nucleic acid substrates may be obtained from oligonucleotide assembly reactions, other assembly steps, amplification reactions, clones, or any other suitable source as the invention is not limited in this respect. In some embodiments, an engineered nuclease can be used in a nucleic acid assembly procedure that includes a series of assembly steps. Engineered nucleases can be used at one or more stages to process a nucleic acid product from a first assembly step for subsequent assembly in a second step that produces a larger nucleic acid product. Aspects of the invention can be useful to generate fragments with termini that include specific single strand overhangs (e.g., 3' or 5' overhangs) for subsequent ligation or cloning. In some embodiments, the overhangs include only sequences of a target nucleic acid being assembled and do not include sequences of a flanking region that contains the nucleic acid motif recognized by the binding domain of the engineered nuclease.

In some embodiments, a design strategy for a nucleic acid assembly procedure involves analyzing the sequence of a target nucleic acid to be assembled to determine whether it contains restriction sites for one or more nucleases that may be used during assembly. In certain embodiments, the presence of certain sites may result in unwanted cleavage products that can interfere with correct assembly. Accordingly, a sequence may be designed to remove unwanted cleavage sites. Alternatively, or additionally, an assembly procedure may be designed to use one or more nucleases (e.g., one or more engineered nucleases of the invention) that do not cut within the sequence of the target nucleic acid.

Aspects of the invention also relate to vectors and other nucleic acid molecules that include sequence motifs recognized by an engineered nuclease and that can be used in one or more nucleic acid assembly steps described herein.

Accordingly, aspects of the invention relate to engineered nucleases, assembly strategies, sequence designs, and/or nucleic acid constructs adapted for use with the engineered nucleases. It should be appreciated that a design strategy may involve modifying a target nucleic acid sequence, selecting an appropriate engineered nuclease that does not cut a target nucleic acid sequence, selecting an appropriate nucleic acid vector or vehicle for use during assembly, or any combination thereof.

In some embodiments, an engineered nuclease includes a cleavage domain that is derived from a Type IIS nuclease.

In some embodiments, an engineered nuclease includes a binding domain that is derived from a restriction enzyme that specifically recognizes a long sequence motif (e.g., 8 bases or more). In some embodiments, the binding domain is derived from a modified restriction enzyme (e.g., a modified meganuclease) that binds to a specific sequence motif but has no nuclease activity (it is nuclease-activity deficient) and does not cleave a bound nucleic acid.

Accordingly, aspects of the invention relate to an engineered chimeric endonuclease comprising a nucleic acid binding domain of a first endonuclease linked to a nucleic acid cleavage domain of a second endonuclease, wherein the nucleic acid binding domain binds a recognition sequence motif recognized by the first endonuclease and is free of an active catalytic domain of the first endonuclease, and wherein the nucleic acid cleavage domain cleaves at a unique cleavage position outside of the recognition motif.

In some embodiments, the nucleic acid binding domain is a DNA binding domain, binds to a double-stranded recognition sequence motif, binds specifically to a unique double-stranded recognition sequence motif, binds selectively to several related recognition sequence motifs, binds with nanomolar affinity to a target nucleic acid comprising the recognition sequence motif, or any combination thereof In some embodiments, the recognition sequence motif has a length of 8 to 10, 10 to 20, 20 to 40, 40-100, or 100-200 nucleotides.

In some embodiments, an engineered chimeric endonuclease, further comprises an inactive mutant catalytic domain of the first endonuclease. For example, the nucleic acid binding domain of the first endonuclease may comprise the inactive mutant catalytic domain. In some embodiments, the nucleic acid binding domain comprises a meganuclease nucleic acid binding domain. In some embodiments, the first endonuclease is a meganuclease variant, and the inactive mutant catalytic domain comprises a catalytic site having one or more amino acid substitutions that inactivate the catalytic endonuclease activity.

In certain embodiments, the endonuclease variant is an inactive intron-coding homing endonuclease (e.g., a "LAGLI-DADG" endonuclease, a "His-Cys" Box endonuclease, a "GIY-YIG" endonuclease, or a "HNH" endonuclease). In some embodiments, the nucleic acid binding domain comprises an inactive I-SceI, I-SceII, I-DmoI, I-CreI, I-CeuI, PI-SceI, I-Ppo, I-TevI, I-TevII, I-TevIII, I-CeuI, or PspI binding domain. In some embodiments, an inactive variant I-Sce endonuclease comprises an N at position 44 and an A at position 145, an inactive variant I-Sce endonuclease comprises an A at position 44 and an A at position 145, and/or an inactive variant I-Cre endonuclease comprises an N at position 20 and an A at position 47.

In some embodiments, the cleavage domain comprises at least one catalytic domain of a Type IIS endonuclease. In some embodiments, the cleavage domain comprises two identical catalytic domains or two different catalytic domains. In certain embodiments the cleavage domain comprises a catalytic domain from a BstF5 I, BtsC I, BsrD I, Bts I, Alw I, Bcc I, BsmA I, Ear I, Mly I, Ple I, Bmr I, Bsa I, BsmB I, Fau I, Mnl I, Sap I, Bbs I, BciV I, Hph I, Mbo II, BfuA I, BspCN I, BspM I, SfaN I, Hga I, BseR I, Bbv I, Eci I, Fok I, BceA I, BsmF I, BtgZ I, BpuE I, Bsg I, Mme I, BseG I, Bse3D I, BseM I, AclW I, Alw26 I, Bst6 I, BstMA I, Eam1104 I, Ksp632 I, Pps I, Sch I, Bfi I, Bso31 I, BspTN I, Eco31 I, Esp3 I, Smu I, Bfu I, Bpi I, BpuA I, BstV2 I, AsuHP I, Acc36 I, Lwe I, Aar I, BseM II, TspDT I, TspGW I, BseX I, BstV1 I, Eco57 I, Eco57M I, Gsu I, or a Bcg I Type IIS endonuclease. In some embodiments, the cleavage domain comprises at least one catalytic domain of a Fok I restriction endonuclease. In some embodiments, the cleavage domain comprises the at least one catalytic domain of a FokI restriction endonuclease associated with at least one portion of a DNA recognition subdomain of the FokI restriction endonuclease. In some embodiments, the nucleic acid binding domain and the nucleic acid cleavage domain are covalently linked without an intervening synthetic peptide linker.

In some embodiments, the nucleic acid binding domain is N-terminal to the nucleic acid cleavage domain. However, the nucleic acid binding domain may be C-terminal to the nucleic acid cleavage domain. In some embodiments, the nucleic acid binding domain and the nucleic acid cleavage domain are linked via an intervening peptide linker (e.g., synthetic or natural). The peptide linker may have a length of 1-5, 5-10, 10-15, 15-20, 20-30, 30-40, or more than 40 amino acids.

Aspects of the invention also relate to recombinant nucleic acids and/or host cells (e.g., eukaryotic, prokaryotic, mammalian, yeast, bacterial, insect, etc.) encoding one or more chimeric nuclease of the invention.

Other features and advantages of the invention will be apparent from the following detailed description, and from the claims. The claims provided below are hereby incorporated into this section by reference.

BRIEF DESCRIPTION OF THE FIGURES

FIGS. 4a and 4c illustrate an engineered endonuclease before binding to DNA (SEQ ID NO: 3) and FIGS. 4b and 4d illustrate an engineered endonuclease bound to DNA (SEQ ID NO: 3);

FIG. 5b illustrates the expression level of soluble I-SceI mutants (SEQ ID NO: 7 NNNNAT-TACCCTGTTATCCCTANNNN; SEQ ID NO: 8 NNNNTAGGGATAACAGGGTAATNNNN; SEQ ID NO: 9 NNNNGGATGNNNNNNNNNNNNNNNNN; SEQ ID NO: 10 NNNNNNNNNNNNNNNNNCATCCNNNN; SEQ ID NO: 11 NNNNATTACCCTGTTATCCCTANNNNNNNNN; SEQ ID NO: 12 NNNNNNNNNTAGGGATAACAGGG-TAATNNNN);

FIG. 6a illustrates the cleavage assay of a linear double stranded DNA containing the native I-SceI recognition site (S) by wt I-SceI into 2 products (P) and the non cleavage of the linear double stranded DNA by Sce7, FIG. 6b illustrates the binding of the Sce7 to DNA, FIG. 6c illustrates the determination of the dissociation constant of Sce7;

DETAILED DESCRIPTION OF THE INVENTION

Figure 1:
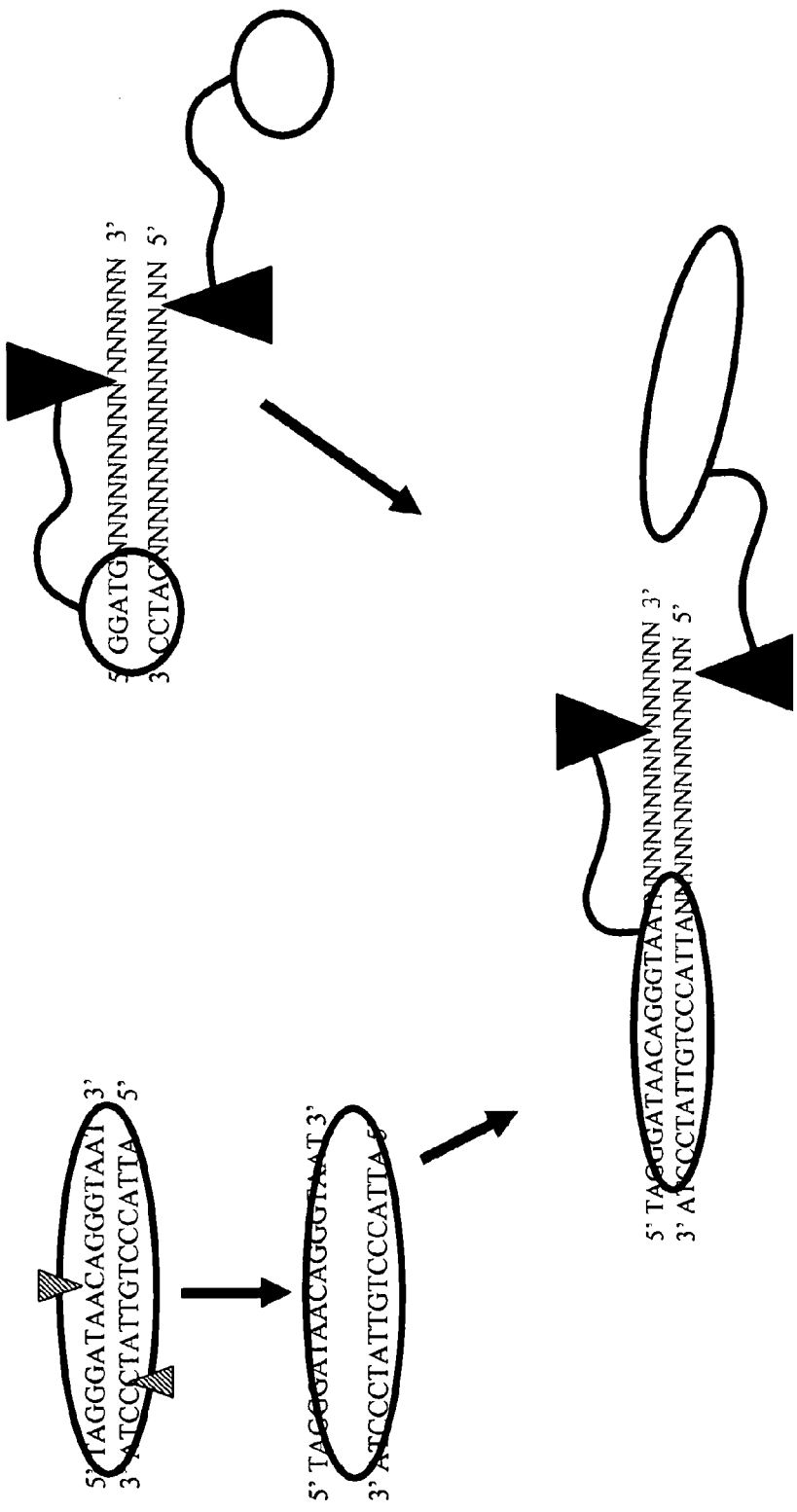
FIG. 1 illustrates a non-limiting embodiment of a method for generating an engineered endonuclease (SEQ ID NO: 1 TAGGGATAACAGGGTAAT; SEQ ID NO: 2 ATTACCCT-GTTATCCCTA; SEQ ID NO: 3 TAGGGATAACAGGG-TAANNNNNNNNNNNNNN; SEQ ID NO: 4 NNNNNNNNNNNNNNNATTACCCTGTTATCCCTA; SEQ ID NO: 5 GGATGNNNNNNNNNNNNNNN; SEQ ID NO: 6 NNNNNNNNNNNNNNNCATCC)
Figure 2:
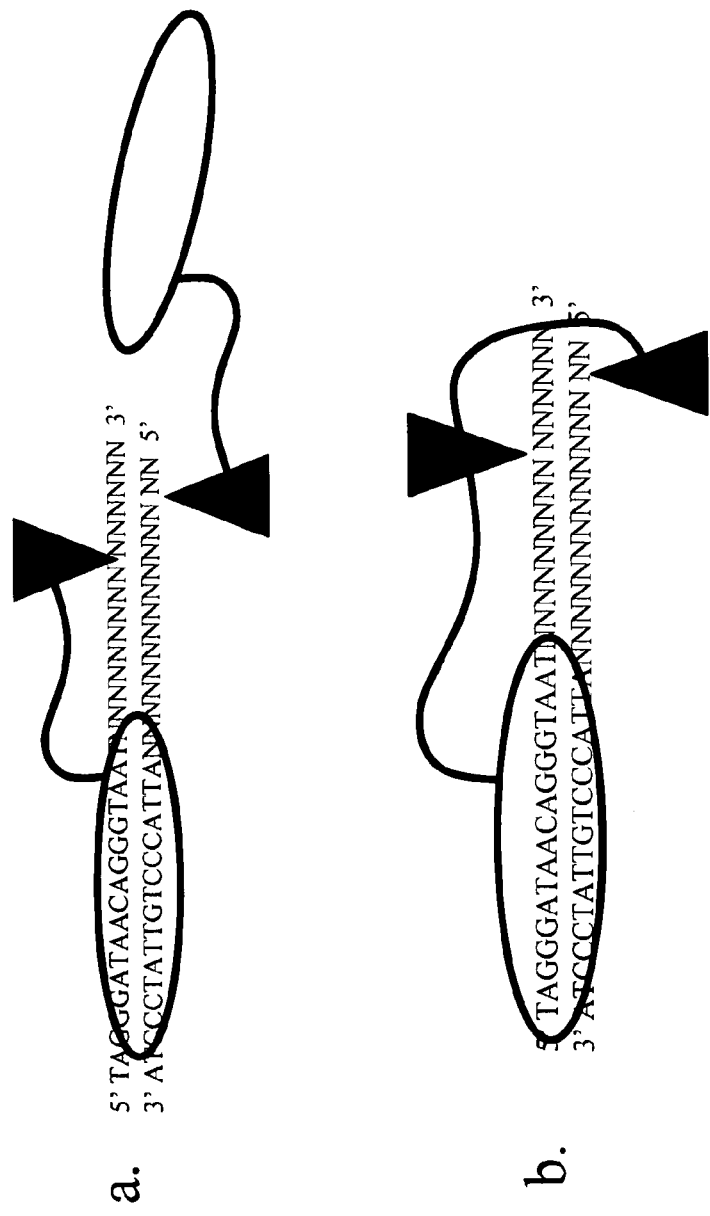
FIG. 2 illustrates a non-limiting embodiment of a mechanism of action with one or two catalytical domains (SEQ ID NO: 5 GGATGNNNNNNNNNNNNNNN; SEQ ID NO: 6 NNNNNNNNNNNNNNNCATCC)
Figure 3:
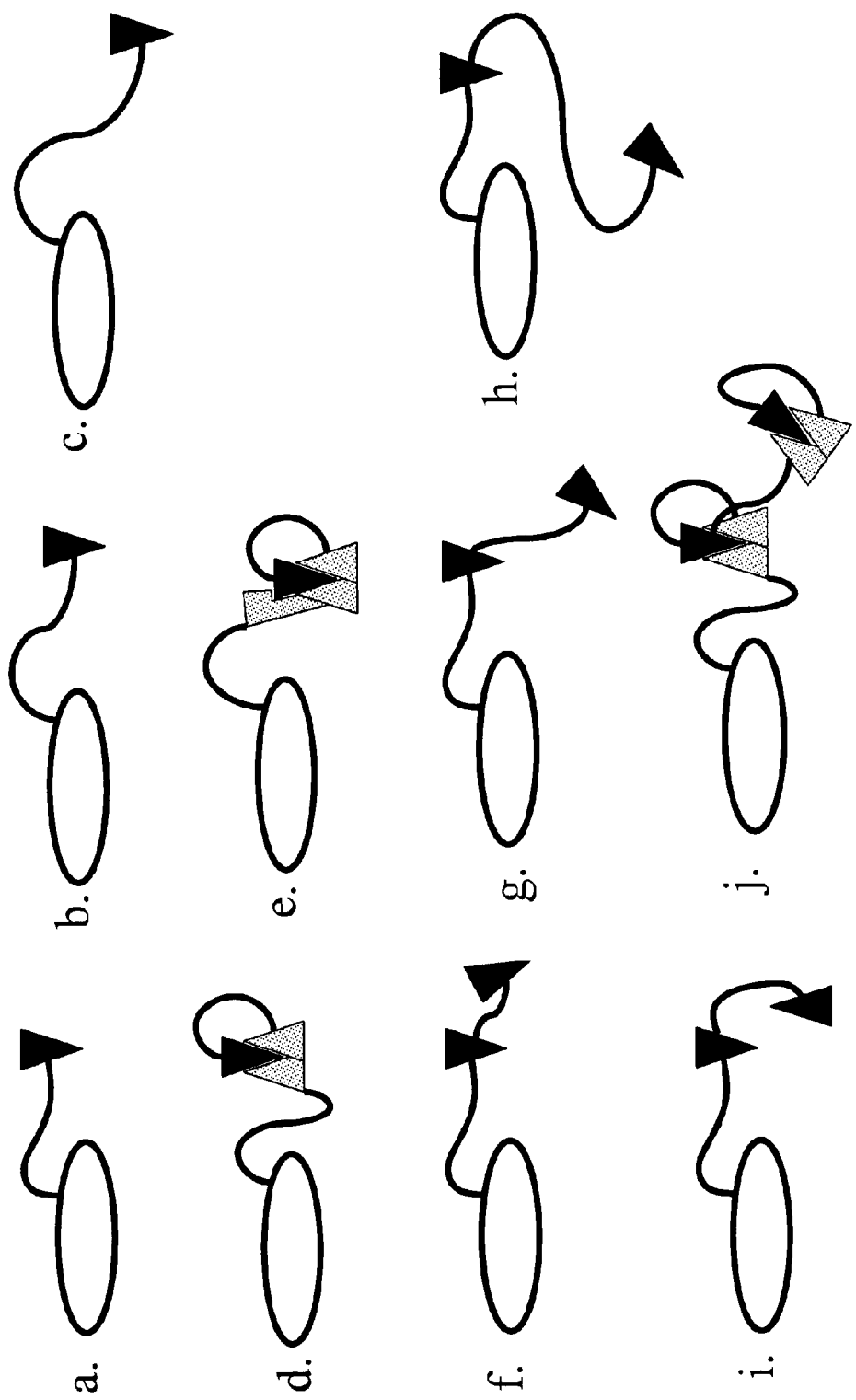
FIG. 3 illustrates non-limiting embodiments of different potential constructs of engineered endonucleases.
Figure 4:
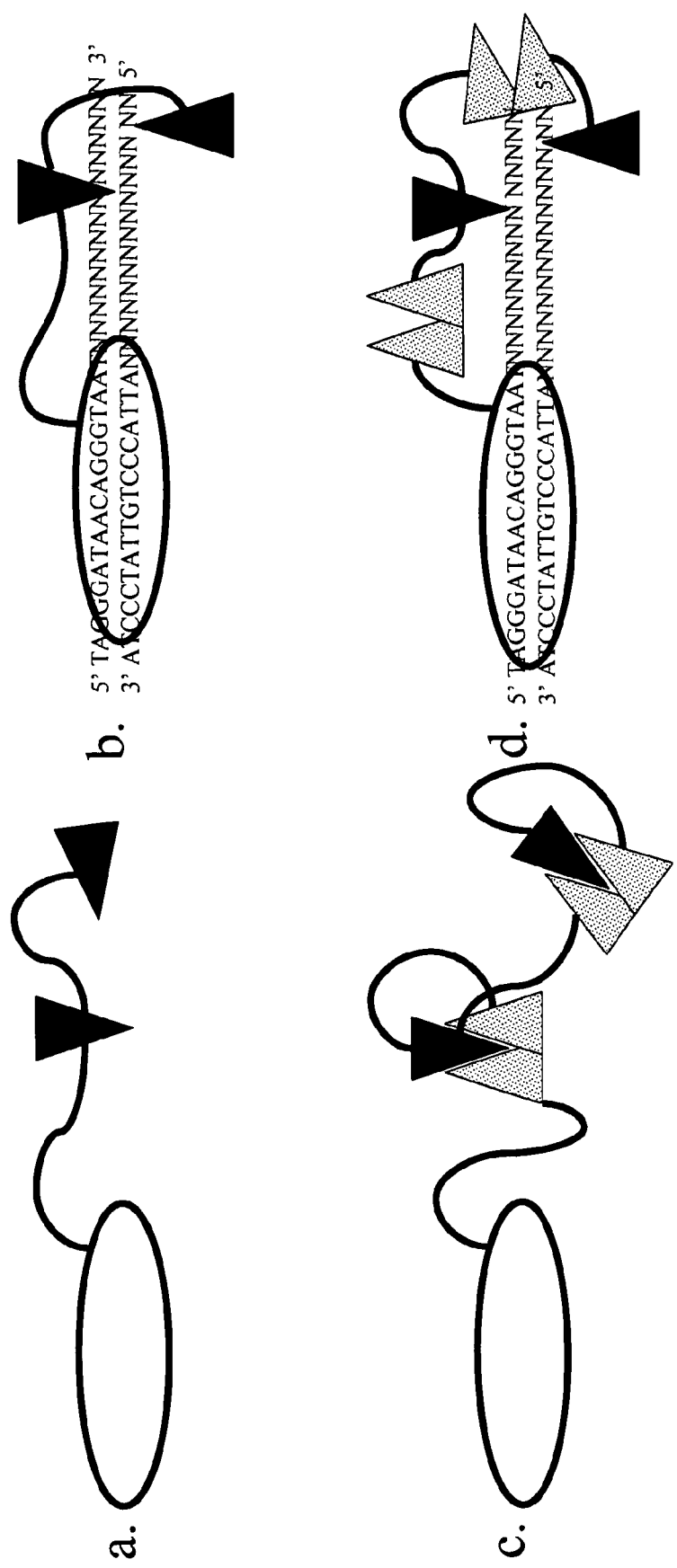
FIG. 4 illustrates non-limiting embodiments of engineered endonucleases with two catalytical domains with or without sequestration domains (D2, D3)

Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

Aspects of the invention relate to compositions and methods for cleaving nucleic acids at predetermined positions regardless of the nucleic acid sequences at the cleavage sites. Aspects of the invention relate to nucleases that are useful for manipulating nucleic acid constructs. In particular, aspects of the invention relate to nucleases that are useful for use in nucleic acid assembly reactions. "Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide. The nucleotide sequences are displayed herein in the conventional 5'-3' orientation.

Methods and composition of the invention can be used to cleave nucleic substrates and generate nucleic acid fragments having cleaved termini at predetermined positions within any sequence of interest. More particularly, methods and composition of the invention can be used to target a cleavage reaction to a unique position within a long nucleic acid substrate (e.g., 5 kb, 10 kb, 20 kb, 50 kb, 100 kb, 1 Mb or longer). Aspects of the invention can increase the efficiency and accuracy of nucleic acid assembly procedures that involve one or more nucleic acid fragment assembly steps. Nucleic acid assembly reactions can involve manipulating large nucleic acid fragments and/or large numbers of nucleic acid fragments. According to the invention, nucleases that can cut at rare positions and/or at positions that are not dependent on the sequence being cut may be useful to manipulate nucleic acids being assembled. Rare motifs recognized by the rare cutting enzymes may be included on assembly constructs (e.g., intermediate nucleic acid assembly constructs) and not be present or only rarely present on the nucleic acids being assembled.

Attempts to alter the specificity of restriction endonucleases by modifying an enzyme's recognition domain have been reported. Nucleic acid binding domains isolated from one protein have been linked to a domain from another protein that exhibits nuclease activity. For example, the FokI endonuclease DNA binding domain (Li et al., 1992; Li et al., 1993) has been fused to the *Drosophila* Ubx homeodomain, to zinc-finger DNA binding domains, and to the yeast Gal4 DNA binding domain (Kim et al., 1994: Kim et al., 1996; Huang et al., 1996; Kim et al., 1998). The most important group of chimeric nucleases includes the Zinc finger nucleases. In one approach, a multi-zinc finger protein capable of binding extended DNA sequences is engineered wherein each zinc finger binds from two to four base pairs of DNA and is linked to the next finger by a short peptide linker (see Durai et al., (2005, Nucleic Acid Research Vol. 33, pp 5978-5990). However, it has been shown that the engineered zinc fingers do not always bind specifically to their cognate DNA triplets but also bind to degenerate sites. Also, the selection of zinc finger binding to a specific DNA site is too labor intensive and cumbersome. Moreover, in order for a multi-zinc finger to specifically target a gene of interest only once within, for example, the human genome, the target site sequence needs to be at least 16 bps, i.e., a 6 finger-protein (Liu et al., (1997) Proceedings of the National Academy of Sciences (USA) 94:5525). However, it has been found that adding more fingers to a 3-finger domain (i.e., about a 9 bp recognition motif) does not yield an increase in specificity and binding affinity, due probably to steric interference when more than three fingers are used, and to non specific contact with the target DNA. Therefore, a need exists for developing a nuclease that binds specifically and with high affinity to a rare DNA site and that cleaves at positions independent of the sequence being cut, particularly for nucleic acid assembly.

Aspects of the invention include generating chimeric engineered endonucleases containing a nucleic acid binding domain and a nucleic acid cleavage domain. In a preferred embodiment, the nucleic avid cleavage domain is outside the nucleic acid binding domain. As used herein, the term "endonuclease" refers to an enzyme which makes a break in a nucleic acid (e.g., a double-stranded break in a DNA molecule) at highly specific locations. Endonucleases comprise a recognition domain and a cleavage domain. As used herein, an "endonuclease recognition site" refers to a nucleic acid sequence capable of binding one or more endonucleases. The term "endonuclease cleavage site" refers to a nucleic acid sequence that is cleaved by one or more endonucleases. For a given endonuclease, the endonuclease recognition and cleavage sites may be the same or different. In a preferred embodiment, the enzyme is a homing endonuclease or a rare-cutting endonuclease that recognizes a nucleic acid motif that is at least 8 base pairs long. As used herein, a "meganuclease" and "homing endonucleases" are used interchangeably. Meganucleases have recognition sequences that span 12 to 45 bps of DNA.

Aspects of the invention include using nucleic acid binding domains from inactive nucleases or deficient nucleases (e.g., nucleases lacking a catalytic activity). As used herein, the term "nuclease activity" includes cleavage of dsDNA, ssDNA, dsRNA, ssRNA, and DNA/RNA duplexes. The inactive nuclease's binding domain can be fused or linked to a cleavage domain as described herein and serve as a sequence-specific recognition domain that promotes site-specific cleavage by the cleavage domain at a predetermined distance from the recognition site.

Aspects of the invention are illustrated in FIGS. 1-9. In some embodiments, a nucleic acid binding domain of a first endonuclease (e.g., a homing endonuclease, a meganuclease, or other endonuclease) that has been modified to reduce or remove catalytic nucleic acid cleavage activity is fused or linked to a nucleic acid cleavage domain of a second endonuclease (e.g., a type IIS endonuclease) to generate an engineered endonuclease that has the specific nucleic acid recognition properties of the first endonuclease (e.g., recognition of a long/rare nucleic acid motif) and the cleavage properties of the second endonuclease (e.g., cleavage on a target nucleic acid outside of the recognition motif). For example, in one embodiment, the homing endonuclease I-SceI, which has an 18 base-pair recognition sequence, was modified into an inactive DNA-binding protein. Using molecular modeling, DNA synthesis, and enzyme characterization, a covalent fusion of the I-SceI mutant and a catalytic domain of the type IIS restriction endonuclease FokI was created. The chimeric protein exhibits the site-specific binding of the homing endonuclease and the cleavage properties of the type IIS restriction endonuclease. However, aspects of the invention are not limited to one particular endonuclease binding domain and one particular type IIS catalytic domain as described in more detail herein.

Nucleic Acid Binding Domains

An engineered nuclease of the invention includes a nucleic acid binding domain. A nucleic acid binding domain may be an RNA binding domain or a DNA binding domain, for example, a single-stranded DNA binding domain or a double-stranded DNA binding domain that recognizes specific target sequences more than 8 base pairs long.

In some aspects, a nucleic acid binding domain may include a polypeptide domain derived from a naturally occurring (e.g., wild type) or non-naturally occurring (e.g., engineered) nucleic acid binding protein. As used herein the term wild type refers to any allelic variant found in nature (e.g., any functional variant found in nature that has binding and/or cleavage activity). In some embodiments, a nucleic acid binding domain may be derived from a natural or synthetic nuclease (e.g., endonuclease) binding domain. In some embodiments, a nucleic acid binding domain may be derived from a restriction endonuclease binding domain. As used herein, restriction enzymes include, but are not limited to, type I enzymes, type II enzymes, type IIS enzymes, type III enzymes and type IV enzymes. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts R J et al. (2005) REBASE—restriction enzymes and DNA methyltransferases. Nucleic Acids Res. 33 Database Issue: D230-2).

Restriction endonucleases cleave DNA with extremely high sequence specificity and due to this property they have become indispensable tools in molecular biology and molecular medicine. Over three thousand restriction endonucleases have been discovered and characterized from a wide variety of bacteria and archae. Comprehensive lists of their recognition sequences and cleavage sites can be found at REBASE. As used herein, the term "specificity" refers to the ability of the endonuclease to recognize (recognition site specificity) and cleave (cleavage specificity) double stranded DNA molecules only at a particular nucleic acid sequence or set of nucleic sequences referred as "recognition sequence" or "recognition site" or "recognition motif". DNA cleavage by the endonuclease may occur within or outside of the recognition sequence. The specificity of a restriction enzyme may be defined by several components: the recognition site (the DNA sequence recognized by the enzyme), the cleavage site (the DNA sequence cut by the enzyme), its catalytic activity (its mode of cleavage), and its sensitivity to DNA modifications within the recognition sequence. For example, the substrate specificity of a restriction endonuclease may involve a single recognition sequence (e.g., BamHI 5'-GGATCC-3') or a degenerate sequence (e.g. BstYI recognizes 5'-RGATCY-3' where R=A or G and Y=C or T). Statistically, an enzyme recognizing a single recognition sequence cleaves a target nucleic acid at a frequency lower than an enzyme recognizing a degenerate sequence. For example, an enzyme recognizing a 6-bp sequence cleaves every 4096 bp while an enzyme recognizing a degenerate sequence cleaves every 1024 bp on average in a genome. Also, it should be appreciated that endonucleases may differ in their level of specificity and their tolerance to changes in their recognition sites. Because the meganucleases have evolved to recognize only one site in a genome they may be able to recognize such a recognition site despite one or more nucleotide changes in the recognition site (that may be due to evolutionary changes). For example, its is known that I-SceI can tolerate many single mutations in its native 18 bp recognition sites rendering its overall specificity to less than the predicted one in $4^{18}$ ($10^{10}$) to an estimated one in $10^7$ base pairs (Jurica and Staddard, 1999, Cell Mol. Life Sci. 55:1304-1326). In some embodiments, the endonuclease binding domain is modified to decrease or remove nuclease activity but retain nucleic acid binding properties (e.g., sequence specific nucleic acid binding properties). The binding domain may be modified relative to a wild type endonuclease or to a variant endonuclease. One should appreciate that because enzyme activity may be correlated to nucleic acid binding activity, modifying the amino acids involved in the nuclease activity can increase or decrease the nucleic acid binding affinity and the degree of recognition specificity (or degeneracy) for the recognition site. As used herein the term "binding affinity" refers to the tendency of an endonuclease to associate in a non-covalent manner to a nucleic acid sequence (e.g., recognition site) and is measured by a dissociation constant $K_D$. In some embodiments, the endonuclease binding domain is modified to decrease or remove nuclease activity and to alter (e.g., decrease or increase) the specificity and/or affinity of the modified binding domain to the recognition site. In some embodiments, the endonuclease binding domain is modified to reduce the nuclease activity without reducing the nuclease activity (e.g., as assayed using an in vivo or in vitro nucleic acid substrate cleavage assay).

A nucleic acid binding domain may be derived from any suitable endonuclease, including a type I endonuclease, a type II endonuclease, a meganuclease, or other endonuclease (e.g., any other sequence specific endonuclease). In a preferred embodiment, a nucleic acid binding domain is derived from a rare-cutting or very-rare cutting endonuclease. Most restriction enzymes are capable of recognizing specific target DNA sequences four to six bases long. The length of the recognition sequence dictates how frequently the enzyme will cut in a random sequence of DNA. Enzymes with a 6 bp recognition site (e.g., EcoRI) will cut, on average, every $4^6$ or 4096 bp; a 4 bp recognition site will occur roughly every 256 bp. A rare-cutting endonuclease (e.g., NotI) which recognizes a 8 bp long recognition sequence will cleave once every $6\times10^4$ bp. A very rare cutting endonuclease, whose recognition specificity requires, for example, 18 bp, will cut only once in every $7\times10^{10}$ bp of random sequence. If the recognition site is not palindromic, or symmetric, then the frequency of cutting will increase two-fold since the recognition site may be found on either strand of double-stranded DNA. A rare-cutting or very rare-cutting endonuclease may be a naturally occurring or synthetic meganuclease, a homing endonuclease, or other rare-cutting endonuclease.

In some embodiments, the nucleic acid binding domain may be derived from an endonuclease that specifically binds to a nucleic acid motif (e.g., an RNA motif, a single-stranded DNA motif, or a double-stranded DNA motif) that is longer than 8 nucleotides, longer than 9 nucleotides, longer than 10 nucleotides, 10-15 nucleotides (e.g., 10, 11, 12, 13, 14, or 15 nucleotides), 15-20 (e.g., 15, 16, 17, 18, 19, or nucleotides), 20-25 nucleotides, 25-30 nucleotides, 30-40 nucleotides, 40-50 nucleotides or longer. Accordingly, a recognition motif may be a 10-15 base pair motif, a 15-20 base pair motif, a 20-30 base pair motif, or a longer double stranded nucleic acid motif.

Thus far, only 25 rare-cutting enzymes are known whose recognition specificities require 8 bp. They represent 12 different nucleotide sequences, among which true palindromes (Qiang B.-Q. and Schildkraut, I. (1987), Nelson J. M. et al. (1990), Kotani H. et al. (1990), Simcox T. G. et al. (1991), Lechner M. et al. (1992), Kappelman J. R. et al. (1995)), interrupted palindromes (Qiang B.-Q. and Schildkraut, I. (1984)) or palindromes with degenerate positions have been found. In some embodiments, a nucleic acid binding domain may be derived from Not-I, Sfi-I, Fse-I, Sse 83871, Srf-I, Swa-I, Sgf-I, Sda-I or FspA-I. In certain embodiments, a nucleic acid domain is derived from a very rare-cutting endonuclease. Accordingly, nucleic acid binding domains may be derived from very rare-cutting endonucleases, for example: I-Ceu I, I-Cre I, I-Chu I, I-Csm I, I-Dmo I, I-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, Not-I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, Pi-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev III, F-Sce I, F-Sce II (HO), F-Suv I, F-Tev I, or F-Tev II.

In one embodiment, restriction enzymes with longer recognition sites (e.g., meganucleases) may be used. As used herein "meganuclease" refers to a homing endonucleases encoded by introns ORF, independent genes, or intervening sequences (inteins) and is used to refer to monomeric meganucleases, dimeric meganucleases, or to the monomers that associate to form a dimeric meganucleases. Meganucleases have recognition sequences that span 12 to 45 bps of DNA. Examples of meganucleases are homing endonucleases, which may be found in phages, bacteria, archaebacteria and various eukaryotes (see for example Epinat et al., 2003, Nucleic Acids Research, 31(11):2953-2962; the entire contents of which are herein incorporated by reference). Meganucleases are characterized structurally and mechanistically and fall into at least 4 separate families on the basis of the amino acids motifs: the "LAGLIDADG", "GIY-YIG", "His-Cys", and "HNH" motif families (see Chevalier and Stoddard, 2001 for review on homing endonucleases). Some meganucleases do not have specific identified motifs and are sometimes referred to as "no-motif" meganucleases. Most of the meganucleases cleave the two strands of a double-stranded DNA and leave a 4 base pair, 3' protruding end. The Dodecapeptide family (e.g., "LAGLI-DADG" family) is the largest family of proteins with more than 150 sequences clustered by their most general conserved sequence motif, with one or two copies of a twelve-residue sequence. Meganucleases with one dodecapeptide are around 20 kDa in molecular mass, and act as homodimers. Those with two copies range from 25 kDa to 50 kDa, with 70 to 150 residues between each motif, and act as monomers. The "LAGL-IDADG" family is characterized by one dodecapeptide motif or two dodecapeptide motifs and a cleavage inside the recognition site, leaving a 4 nucleotide staggered cut with 3'OH overhangs. One dodecapeptide motif meganucleases include, but are not limited to, I-Ceu I, and I-Cre I. I-Cre-I, for example, recognizes the 22 bp nucleic acid motif SEQ ID NO 25: CTGGGTTCAAAACGTCGTGAGACAGTTTGG (−10/−14) and generates a 4 nucleotide staggered cut with 3'OH overhangs. Two dodecapeptide motif meganucleases include, but are not limited to, I-Chu I, I-Csm I, I-Dmo I, I-Pan I, I-Sce I, I-Sce II, I-Sce II, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, and PI-Thy II. I-Sce-I, for example, recognizes the 18 bp nucleic acid motif: SEQ ID NO 26: AGTTACGCTAGGGATAACAGGGTAATATAG (−13/−17) and generates a 4 nucleotide staggered cut with 3'OH overhangs.

The GIY-YIG family has a well conserved joint motif "KSGIY (10/11 AA) YIGS" and a cleavage site that is different from the recognition sequence and outside the recognition site leaving a 2 nucleotide staggered cut with 3'OH overhangs. Some examples are I-Ncr I, I-Ncr II, I-Pan II, and I-Tev I. The I-TevI endonuclease has a N-terminal catalytic domain and a C-terminal DNA-binding that are connected by a flexible linker. The C-terminal binding domain recognized a 20 bp sequence and the cleavage site is about 25 bps away (Derbyshire et al. 1997, J. Mol. Biol. 265:494-506). The DNA binding domain comprises 3 separate DNA-binding subdomains: a zinc finger, an alpha-helix and a helix-turn-helix domain. In some embodiments, the catalytic domain of TevI may be used as the basis of a catalytic domain of an engineered nuclease of the invention. In some embodiments, the TevI recognition site may be modified and screened to identify mutated TevI endonucleases having a different recognition site than the natural endonuclease and retaining a catalytic activity. In some embodiments, a type IIS cleavage domain may be attached to a TevI recognition site or variant thereof. Similarly, any other member of the GIY-YIG family or other appropriate family of endonucleases may be used to obtain a catalytic (and/or nucleic acid binding) domain for chimeric endonucleases of the invention. Any other member of the GIY-YIG family or other appropriate family of endonucleases may be linked to a type IIS cleavage domain. In some embodiments, sequence variants of any other member of the GIY-YIG family or other appropriate family of endonucleases may be varied and screened to identify variant endonucleases that bind to different long recognition sequences. These nucleic acid binding domains of these variant endonucleases could then be used according to methods of the invention. In some embodiments, a natural endonuclease linker (for example comprising the TevI linker: 120-MLKLGPDGRKALYSKPGSKN-140, or a protease resistant variant or a portion of either thereof) may be used as a linker to connect one or more different nucleic acid binding domains, cleavage domains, or any other domains described herein.

The "HC" or "His-Cys" family have sequences rich in Histidines and Cysteines and the conserved sequence is approximately: "SHLC-G-G-H-C". Cleavage is inside the recognition site, leaving a 4 nucleotide staggered cut with 3'OH overhangs. The most well characterised enzyme is I-Ppo I. The "HNH" family has the "HH-N-H—H" consensus sequence in a window of 35 amino acid residues (e.g., I-Tev-III). They cleave double-stranded DNA inside the recognition site and leave a 5' extension of 2 nucleotides after a double-stranded break.

The no motif family is characterized by a cleavage of long size of staggered cut of at least 10 nucleotides (e.g., I-Dir I, I-Hmu I, I-Hmu II).

Meganucleases can be encoded by "free" genes (see, for example F-Sce I, F-Sce II (HO), F-Suv I, F-Tev I, and F-Tev II) or inteins.

In one aspect of the invention, a nuclease nucleic acid binding domain may be derived from an inactive variant of a nuclease (e.g., a naturally occurring mutant or polymorphic inactive variant, or an experimentally or synthetically produced inactive variant of a nuclease). The inactive variant may, for example, be one that substantially or completely retains nucleic acid binding properties but has reduced nuclease activity.

In certain embodiments, a nucleic acid binding domain may be isolated from a nuclease and introduced into a new polypeptide framework. The nuclease activity may be removed in the context of the new polypeptide framework. Non-limiting methods for inactivating nucleases and/or removing nuclease activity are described herein and may include methods for screening or selecting nuclease deficient nucleic acid binding proteins. As used herein, a nuclease deficient protein or an inactive nuclease has less than 50%, less than 75%, less than 80%, less than 90% less than 95%, less than 99% of the activity of the wild type nuclease. In one embodiment, the inactive nuclease has no catalytic activity.

A nuclease deficient nucleic acid binding domain may include one or more amino acid substitutions, insertions, deletions, duplications, or any combination of two or more thereof, relative to a nucleic acid binding domain that has nuclease activity. As used herein an "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and —O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

In one aspect of the invention, endonuclease variants are prepared by targeted mutagenesis of an initial endonuclease by introducing mutations at positions implicated in the endonuclease's catalytic activity. The residues within the catalytic sites of rare-cutting meganucleases may be identified based on the structure determined by X-ray crystallography. To date, the three dimensional structures of the homing endonuclease I-Dmo-I, PI-Sce-I (Moure et al., 2003, J. Mol. Biol. 334: 685-695), PI-Pfu-I (Ichiyanagi et al., 2000), I-Cre-I (Heath et al., 1997), I-Ppo-I (Flick et al. 1998) and I-Tev-I (VanRoey et al., 2001) are known. In some embodiments, the residues within the catalytic domain of I-Sce I or I-Cre I homing endonucleases are targeted.

For example, residues D44 and D145 of Sce-I are identified as part of the catalytic domain based on the Sce-I crystal structure (Doyon et al., 2006, J. Am. Chem. Soc. 128: 2477-2484)) and residues D20, Q47, R51 and R70 are identified as part of the catalytic domain based on the Cre-I crystal structure (Chevalier et al., 2001). The crystal structure of I-SceI in complex with DNA shows the side chain of D44 and D145 interacting with two backbone phosphate groups but not with the DNA bases (Moure et al., 2003). In one exemplary embodiment of the present invention, a set of I-Sce I variants is prepared by introducing amino-acid diversity at D44 or D145 or any combination thereof. In one embodiment, both residues are mutated. For example, mutations may be introduced to change D44 into N44 or D44 and D145 into A145 or D145, respectively. In another embodiment, I-Cre I variants are prepared by introducing amino acid diversity at one or more positions selected from the group consisting of D20, Q47, R51 or R70 or any combination thereof. Amino acid diversity may include one amino acid variation, or any combination of two or more thereof. In one embodiment, amino acids D20 and Q47 are mutated into N20 and A47, respectively. Endonuclease variants may be generated using any suitable methods (e.g., targeted mutagenesis, random mutagenesis, DNA shuffling, directed mutagenesis, PCR assembly, or by a combination thereof). Preferably, one or more residues may be targeted for site-specific mutagenesis. Site-specific mutagenesis may be performed using a defined oligonucleotide to create a specific substitution or a degenerate oligonucleotide to create a variety of different substitutions. One should appreciate that in some instance, if the crystal structure of the endonuclease to be modified is not known, the residues responsible for the catalytic activity cannot be identified with confidence. In this case, non-targeted mutagenesis can be achieved by any method known in the art, for example, random mutagenesis, error-prone PCR, chemical mutagenesis, etc., or any combination thereof.

In a preferred embodiment, inactive endonucleases are screened and selected based on their capacity to bind a target DNA sequence and their inability to cleave the targeted sequence. In some embodiments, meganuclease variants that bind a target DNA sequence with an affinity and specificity comparable to wild type, but do not cleave the targeted DNA sequence, are selected. Some variants are selected for their ability to bind a target DNA sequence with an affinity equal to or higher than wild type endonuclease, and for their inability to cleave DNA. In some embodiments, the inactive endonuclease variants can adopt a conformation which improves the interaction with DNA recognition sites. For example, affinity of the variants for the DNA recognition site may be twice, three times, 5 times, or 10 times higher than wild type. In one embodiment, the selected variants are thermostable. However, it should be appreciated that in some embodiments a variant may an affinity for its recognition sequence motif that is less than the wild-type affinity and nonetheless retain sufficient affinity.

In some embodiments, an engineered nucleic acid binding domain may include a plurality of copies of a binding domain (e.g., 2, 3, 4, 5, 6, 7, 8, 9, 10 or more copies of a binding domain). In certain embodiments, a plurality of copies of the same nucleic acid binding domain may be combined. In some embodiments, a plurality of different nucleic acid binding domains may be combined. However, it should be appreciated that an engineered nuclease may contain a plurality of different binding domains including a plurality of copies of one or more of the different binding domains. By combining two or more copies of the same or different nucleic acid binding domains, a nuclease may be engineered to recognize a long nucleic acid sequence motif that includes a combination of the motifs recognized by the individual binding domains.

In some aspects, an engineered nuclease may include a nucleic acid binding domain that is a synthetic domain designed to recognize a specific nucleic acid motif. For example, a nucleic acid binding domain may be derived from and/or include one or more naturally occurring or engineered meganucleases, zinc finger proteins, viral replication proteins, α-helical DNA binding proteins, DNA binding moieties of gene transcription factors, repressors, oncogenes, nuclear hormone receptors, TATA binding proteins, leucine zipper type proteins, basic luecine zippers, beta-sheet motif proteins, helix-turn-helix motif proteins, beta-hairpin motifs, homeodomains, replication-terminator proteins (e.g., Tus), or any other DNA binding proteins that recognize more than an 8 base pair recognition site.

In some aspect of the invention, an engineered nuclease may include a modified nucleic acid domain with altered binding specificity and/or affinity for a recognition site relative to the parent endonuclease. As used herein, the term "altered specificity" refers to the ability of endonuclease to bind to recognition site that is not bound by a wild type endonuclease. For example, the engineered nuclease may recognize sequence which differs by at least one by from the wild type endonuclease recognition sequence.

It should be appreciated that a binding domain may include a plurality of binding subunits. In some embodiments, each subunit may have specific binding properties. In certain embodiments, individual subunits do not bind to nucleic acid (e.g., specifically or non-specifically) alone, but do specifically bind to nucleic acid when combined. Accordingly, an engineered binding domain may be a dimer, trimer, tetramer, or other multimer (e.g., a homodimer, a homotrimer, a homotetramer, a homomultimer, a heterodimer, a heterotrimer, or a heterotetramer, or a heteromultimer) of nuclease free nucleic acid binding subunits. Different binding subunits may be linked together (e.g., in single chain polypeptides). Binding subunits may be separated by suitable linkers (e.g., polypeptide linkers). The different binding subunits may be expressed as a single chain polypeptide from a suitable expression construct.

It should be appreciated that a nucleic acid motif recognized by a binding domain may include repeat sequences (e.g., direct or inverted repeats), palindromes, true palindromes, interrupted palindromes, pseudo-palindromes, palindromes with degenerate positions, etc., for example.

Accordingly, a nucleic acid motif may include regions of secondary structure such as hairpin loops, etc., or any combination thereof.

It should be appreciated that aspects of the invention also may be used for nucleic acid binding domains that recognize and bind to sequence motifs that are 8 or less than 8' nucleotides long (e.g., 3, 4, 5, 6, 7, or 8 base pairs or nucleotides long).

Cleavage Domains

Certain type IIS restriction endonucleases (e.g., FokI, and AlwI) and type I restriction endonucleases include different domains or subunits, one or more of which are responsible for sequence specificity and one or more for catalysis. In one aspect of the invention, a chimeric endonuclease is produced by fusing a catalytic domain or a part of a catalytic domain responsible for nucleic acid cleavage (e.g., a type IIS cleavage domain) to a or part of a nucleic acid binding domain from a different protein (e.g., a catalytically inactive nucleic acid binding domain from a meganuclease or other endonuclease). In some embodiments, a type IIS cleavage domain is provided along with an associated sequestration domain (e.g., from the same type IIS enzyme) that prevents the cleavage domain from randomly digesting nucleic acid molecules in a sample. However, the sequestration domain does not prevent the cleavage domain from digesting nucleic acids that are specifically recognized and bound by the binding domain of the chimeric endonuclease.

In some embodiments, a FokI cleavage domain is fused to a nucleic acid binding domain. The best understood type IIS restriction endonuclease is the FokI restriction endonuclease from *Flavobacterium okeanokoites*. FokI recognizes the asymmetric 5 nucleotides long sequence 5'-GGATG-3' and cleaves double-stranded DNA outside the recognition sequence, i.e., at staggered sites 9 and 13 nucleotides away from the recognition site on the 5' and on 3' strand, respectively (Wah, D. A. et al., *Proc Natl Acad Sci USA* 95 (18): 10564-9). The cloning and sequencing of the FokI restriction-modification system have been reported. Several research groups have purified FokI endonuclease and characterized its properties. Fok-I has a modular structure with an N-terminal DNA-binding domain and a C-terminal catalytic domain with non-specific DNA cleavage activity that are connected by a linker region. The N-terminal recognition domain contains three subdomains (D1, D2 and D3; Wah D A et al., Nature, 1997, 88(6637):97-100). DNA cleavage is mediated through the dimerisation of the non-specific cleavage domain (Bitinaite et al., *Proc Natl Acad Sci USA* 95 (18): 10570-5). Also, the Fok I-DNA complex crystal structure shows that the catalytic domain of the endonuclease is bound to the side of the DNA recognition domain instead of to the DNA, revealing a putative mechanism in which the sequestration of the catalytic domain contributes to the specificity of DNA cleavage.

In some embodiments, the cleavage domain of a type IIS restriction enzyme is fused to a DNA binding domain. In some embodiments, the cleavage domain of a type IIS restriction enzyme is fused to part of a DNA binding domain. In one embodiment, the cleavage domain of FokI is fused to a DNA binding domain, for example, an endonuclease binding domain lacking a catalytic activity. It should be appreciated that although most Type IIS endonucleases bind to DNA as monomers, the enzymes cleave double strand DNA through dimerization of the catalytic domains of two monomers. For example, it has been shown that Fok I dimerization is important for active DNA cleavage (Bitinaite et al., 1998). Accordingly, in one aspect of the invention, two type IIS cleavage domains are linked to a DNA binding domain. The two type IIS cleavage domains can be two identical type IIS cleavage domains (e.g., two FokI cleavage domains) or two different cleavage domains from the same or different type IIS endonucleases. In some embodiments, the two cleavage domains are covalently linked by a spacer or linker peptide and fused to a DNA binding domain.

However, it should be appreciated that in some embodiments a linker peptide is not required for connecting two different domains (e.g., two cleavage domains, a nucleic acid binding domain and a cleavage domain, any other domains described herein, or any combination thereof). In some embodiments, two domains may be fused through their natural amino acid sequences without any additional linker sequences. In some embodiments, a linker equal to or longer than a minimal length may be used. The minimum length of the spacer peptide may be modeled according to the minimal physical separation required to avoid steric hindrance of the catalytic domain or the DNA binding domains. Linkers may be designed on the theories of end-to-end distance of flexible polypeptides as a function of the number of residues (Zhou, 2003, J. Mol. Biol. 329:1-8; Zhou, 2004, Biochemistry, 43:2141-2154). For example, a physical separation between the two catalytic domains may be of 55 or more, 60 or more, or 64 or more Angstroms. Spacer peptides can be used to link the two cleavage domains. In some embodiments, the spacer peptide is 25 amino acids (aa) or more, 40 aa or more, or 75 aa or more amino acids in length. It should be appreciated that the flexibility and the hydrophilicity of the spacer peptide is important so as not to disturb the functions of the different domains being fused. Accordingly, the amino acid composition may be varied to increase the degree of flexibility or rigidity of the linker and therefore to create a proper spatial separation of the different domains. For example, by varying the number of Alanine (A) or Proline (P) amino acids, one can modulate the flexibility of the spacer. Moreover, Proline residues may be incorporated into the linker to prevent the formation of significant secondary structural elements by the linker. Also, spacer flexibility can be increased by increasing the number of charged amino acids such as Aspartate (D) or Lysine (K), or other amino acids such as Serine (S) or Glycine (G), in the spacer peptide sequence. Preferred amino acid residues for spacers include, but are not limited to Glycine (G), Serine (S), Aspartic Acid (D), Asparagine (N), Lysine (K), Arginine (R) and Proline (P) and by avoiding amino acids with a preference for α-helix or β-strand secondary structure. The spacers of the present invention can be made by making recombinant nucleic acids encoding the spacer and the two cleavage domains. Instructions sufficient to direct one of skill through such cloning are found in Sambrook, Berger, Ausubel and Innis. Optionally, the spacer also can be made using peptide synthesis, e.g., using a peptide synthesizer, or other solid phase protein synthesis technique and then linked to the two cleavage domains.

It should be appreciated that similar modeling techniques may be used to determine what length of a natural peptide on either domain should be retained to avoid needing a heterologous linker (e.g., synthetic linker or a linker from another natural source) to connect two domains.

In one embodiment, the peptide spacer may be composed of 70% G, 20% S, 5% D, 5% N (S design) or of 30% G, 20% S, 30% D, 5% R, 5% K, 5% N, 5% P (D design) to increase or otherwise optimize its flexibility.

In some embodiments, a 25 amino acid spacer has one of the following amino acid sequences and designs SEQ ID NO: 27 GGSGGGSGDGSGNGGSGGDSGGSGG (25S) or SEQ ID NO: 28 GGSGDRDGSDSDRPDSDKNDDGSGG (25D). In other embodiments, a 40 amino acid spacer peptide may have one of the following amino acid sequences

```
                                                    SEQ ID NO: 29
GGSGGSGGNGGGSGGDGSGRSGGNGGGDGGSGGGSGSGG (40S)
or
                                                    SEQ ID NO: 30
GGSGDGDSKDDSDPRDGDNSGGRDNPDSDGSGSKDDGSGG (40D).
```

In yet in other embodiments, a 75 amino acid spacer may have one the following amino acid sequences:

```
                                                    SEQ ID NO: 31
GGSGGDSGPSGGGNGGSGRDGGGSNGGSRGSGGDSGPSGGGNGGSGGSGK

DGGGNGGSGGKDSGGNGGSGGGSGG (75S)
or
                                                    SEQ ID NO: 32
GGSGDGDSKDGSDPDNGDSRDGGNPGDGSGRDGDGSGDNGDGPSRSDSKS

SDDSDKNPDGDSGDRSDGDKDGSGG (75D).
```

Other examples of linkers and techniques for obtaining suitable linkers for connecting molecules may be found in US2005/0202498, the linker and related techniques descriptions of which are incorporated herein in their entirety.

In some embodiments, the length and/or sequence of natural or linker peptides that are used to connect two or more domains may be optimized to provide sufficient flexibility for cleavage at a single unique site outside of the binding motif on a target nucleic acid, but not result in a degree of flexibility that would result in cleavage at two or more sites near the binding motif. Accordingly, in some embodiments of the invention, a chimeric endonuclease cleaves at a unique position on a target nucleic acid relative to the binding sequence that is recognized by the binding domain of the chimeric molecule.

Accordingly, in some embodiments the DNA binding domain may be fused directly to the catalytical domain. In other embodiments, the physical separation between the catalytic domain(s) and the DNA binding domain(s) may be used to determine the minimum length of the linker needed to connect the N-terminal and C-terminal domains. It should be appreciated that either the nucleic acid binding domain or the cleavage domain may be the N-terminal domain (with either the cleavage domain or the nucleic acid binding domain being the C-terminal domain, respectively). Accordingly, in some embodiments, the physical separation between the catalytic domain(s) and the DNA binding domain(s) may be used to determine the minimum length of the linker (or the length of a natural sequence associated with one or more binding or cleavage domains) needed to connect the C-terminal amino acid of the DNA binding domain of the inactive endonuclease with the N-terminal amino acid of the catalytic domain of the type IIS restriction enzyme, without steric hindrance to the linker, the catalytic domain or the DNA binding domain. This length may then be increased to create a longer linker that avoids introducing strain to the engineered endonuclease. Similar considerations would be applied to embodiments where the C-terminal amino acid of any nucleic acid binding or cleavage domain is being connected to the N-terminal amino acid of any cleavage or nucleic acid binding domain, respectively.

In some embodiments, the linker length and/or composition between the DNA binding domain and the catalytic domain is chosen to allow the cleavage domain to reach and cut at only one position downstream the recognition site. One should appreciate that a DNA binding domain may have extra residues at its C or N terminus and that it may not be necessary to add a linker between the DNA binding domain and the catalytic domain. In some embodiments, the part of the DNA binding domain (e.g., truncated binding domain) may be fused or linked to a catalytic domain. In an exemplary embodiment, the C-terminus of the binding domain of SceI is within 35 angstrom of at least one of the N-termini of the catalytic FokI dimer. Linkers may be designed on the theories of end-to-end distance of flexible polypeptides as a function of the number of residues (Zhou, 2003, J. Mol. Biol. 329:1-8; Zhou, 2004, Biochemistry, 43:2141-2154). In some embodiments, the catalytic domain is linked to a DNA binding domain with a peptide linker that is 1 to 9 amino acids, 10 amino acids or more, 15 amino acids or more, 20 amino acids or more, 30 amino acids or more. In one exemplary embodiment, the catalytic domain of FokI is linked to the DNA binding domain of SceI variant with a peptide linker that is 10 amino acids long, 15 amino acids long, 20 amino acids long. In one embodiment, the composition of the peptide linker is the natural linker segment SEQ ID NO: 33 QFVIPNRGVT-KQLVK that links FokI recognition domain to its cleavage domain (Wah et al., 1998, PNAS pp 10564-10569). It should be appreciated that the flexibility and the hydrophilicity of the linker peptide is important so as not to disturb the function of the different domains being connected. Accordingly, the amino acid composition may be varied to increase the degree of flexibility or rigidity of the linker and therefore to create a proper spatial separation of the binding domain and the cleavage domain. For example, by varying the number of Ala (A) and Pro (P) amino acids, one can modulate the flexibility of the linker. Moreover, Proline residues may be incorporated into the linker to prevent the formation of significant secondary structural elements by the linker. Also, spacer flexibility can be increased by increasing the number of charged amino acids such as Asp (D) and Lys (L), or other amino acids such as Ser (S) and Gly (G), in the linker peptide sequence and by avoiding amino acids with a preference for α-helix or β-strand secondary structure. The linker used to link the DNA-binding domain to the catalytic domain can comprise any amino acid sequence that does not substantially hinder interaction of the DNA-binding domains with their respective target sites. Preferred amino acid residues for linkers of the present invention include, but are not limited to Glycine (G), Serine (S), Aspartic Acid (D), Asparagine (N), Lysine (K), Arginine (R) and Proline (P). In some embodiments, the fifteen residues linker from wild-type FokI (SEQ ID NO: 34 QFVIPNRGVTKQLFVK) is used to link the DNA binding domain to the catalytic domain. Typically, the linkers of the invention are made by making recombinant nucleic acids encoding the linker, DNA-binding domain and the catalytic domain, which are fused via the linker amino acid sequence. In some embodiments, the peptide linkers comprise a Linker10s GGSGGDGSGG aa sequence (SEQ ID NO: 35), a Linker10d GGDSRDSDGG aa sequence (SEQ ID NO: 36), a Linker14s GGSGGSGDGGGSGG (SEQ ID NO: 37), a Linker14d GGDSRDPSDKSDGG (SEQ ID NO: 38), a Linker 20s GGGSGGSDGSGNGGSGSGGG aa sequence (SEQ ID NO: 39), a Linker 20d GGSGDRDDSDPSD-KNDGSGG aa sequence (SEQ ID NO: 40), a Linker 22s GGGSGGSGDGSGNGGSSGSGGG aa sequence (SEQ ID NO: 41), a Linker 22d GGSGDRDGDSDPSDKNDDGSGG aa sequence (SEQ ID NO: 42), a Linker 25s GGSGGGS-GDGSGNGGSGGDSGGSGG aa sequence (SEQ ID NO: 27), a Linker 25d GGSGDRDGSDSDRPDSDKNDDGSGG aa sequence (SEQ ID NO: 28), a Linker 30s GGSGGGS-GDGGSGGGSGGNSGGDGSGGSGG aa sequence (SEQ ID NO: 43), a Linker 30d GGSGDGRDGSDNSGDDRPDS-GDKNDDGSGG (SEQ ID NO: 44), a Linker 40s GGSGGSGGNGGGSGGDGSGRSG-
GNGGGGDGGSGGGSGSGG (SEQ ID NO: 29) or a Linker
40d GGSGDGDSKDDSDPRDGDNSGGRDNPDS-
DGSGSKDDGSGG (SEQ ID NO: 30).

It should be appreciated that in order for FokI to cleave only when bound to the target DNA, FokI catalytic activity may need to be sequestered alongside the recognition domain. Accordingly, in one aspect of the invention, part of a FokI cleavage site or domain may be linked to a portion or the totality of an inactive FokI endonuclease binding domain (or sequestration domain) to reduce non specific cleavage. For example, the sequestration domain may comprise part or the totality of the D1 subdomain, D1D2D3 subdomains or D2D3 subdomains. In one embodiment, the FokI cleavage domain is linked to aa residues 4 to 156 of the FokI D1 subdomain. In another embodiment, the FokI cleavage domain is linked to aa residues 157-372 of the FokI D2D3 subdomains. In further embodiments, part of D1 and/or D2D3 FokI recognition subdomains are mutated to reduce or eliminate FokI DNA binding activity. In some embodiments, a library of D1 mutants is designed to block specific interaction with the target DNA. For example, the D1 mutant library may carry one, two or any combination of the following aa substitutions Q12S, N13S, R79Q, Q95S. In one embodiment, part of or the totality of the mutated D1 subdomain is linked to part or the totality of the D2D3 subdomains. In another embodiment, the D2D3 subdomain comprises a library of D2 mutations designed to block specific interactions with the target DNA. For example, the D2D3 mutant library may carry one, two or more or any combination of the following aa substitutions E220N, K225S, R228Q. In another embodiment, a FokI cleavage domain is linked to part or the totality of D2D3 subdomains or mutated D2D3 subdomains in the absence of a D1 domain. In some embodiments, the hydrophobic amino acids of the natural or mutated D2D3 subdomains are substituted with hydrophilic aa to increase solubility. For example, one or more of L184N, F192Y, I230T, W233K, L234S, L237E, L239N, V274T, V287T, E220N, K225S, R228Q substitutions may be included in the D3 subdomain.

Selection and Screening

DNA binding domain variants may be expressed in *E. coli*, purified and selected in vitro for their ability to bind to a recognition motif of a target nucleic acid and their inability to cleave the target sequence. Screening of variant libraries for the binding ability may be performed on target DNA sequences containing a DNA recognition site. The DNA target sequence length may be less than 200 bp, less than 500 bp, less than 1 kb, less than 10 kb. Binding of the variants to the target nucleic acid may be assessed using methods known in the art, for example gel retardation assays. Densitometry may be performed on a digital image of the gel to determine the relative intensities of the bands corresponding to bound and unbound DNA. Intensities of bound and unbound DNA are used to determine the concentrations of bound and free enzyme at each initial concentration. Binding affinities (dissociation constants, Kd) can be determined by plotting the concentration of bound enzyme on the y-axis and the concentration of free enzyme on the x-axis for each data point and fitting the data to a rectangular hyperbola using standard nonlinear least-squares fitting procedures, using the equation $y=([DNA]*x)/(Kd+x)$. In some embodiments, variants displaying a binding affinity equal to the wild type protein are selected. In some embodiments, variants displaying a binding affinity superior to the wild type protein are selected. For example, I-SceI variants binding to the target DNA with a Kd of less than about 50 nM may be selected, and I-CreI variants binding to the target DNA with a Kd of less than 200 nM may be selected. In general, variants then may be selected for their inability to cleave a target DNA containing the nuclease recognition site. A target DNA sequence may be less than 1 kb, less than 5 kb, or less than 10 kb. For example, the target DNA for a cleavage assay may be a plasmid such as pUC19 containing an insert including the endonuclease recognition site. Nuclease variants that do not cleave DNA under conditions where wild-type nuclease cleaves may be selected. In some embodiments, variants that bind the target DNA and cleave less than 0.5%, less than 1%, less than 2%, or less than 5% target DNA are selected.

DNA binding domain variants fused to a nucleic acid cleavage domain of an endonuclease may be screened and selected in vitro or in vivo. In one embodiment, engineered nucleases may be screened and selected in vitro for their ability to bind to a recognition motif of a target nucleic acid and to cleave the target sequence. Screening of variant libraries for the binding ability may be performed on target DNA sequences containing a DNA recognition site. The DNA target sequence length may be less than 200 bp, less than 500 bp, less than 1 kb, less than 10 kb. For example, the target DNA for a cleavage assay may be a plasmid such as pUC19 containing an insert including the endonuclease recognition site. Engineered nucleases that cleave DNA under conditions where wild-type nuclease cleaves may be selected. One should appreciate that the engineered nucleases of the invention may not have the same optimal cleavage conditions than the "parent" endonucleases from which they are derived. Buffer composition, buffer pH, incubation temperature and/or incubation time can alter the specificity and/or the activity of the engineered nuclease resulting in for example, non-specific degradation of the substrate DNA, cleavage at partially matching recognition sites. In some embodiments, digestion conditions are optimized for each engineered nuclease variant.

One in vivo selection system for detecting homing endonuclease activity is described by Gruen et al. (Nucleic Acids Res., (2002) 30:e29) and links the catalytic activity of a homing endonuclease to the survival of *E. coli* via a DNA cleavage event. This system employs two plasmids, one plasmid encodes a mutant barnase gene with two amber (TAG) stop codons under an inducible arabinose promoter, followed by tandem endonuclease recognition sites. The other plasmid contains nucleic acids encoding a homing endonuclease fused to an Amber suppressor tRNA supE under the constitutive lac promoter. The co-expression of the mutant barnase gene and the tRNA expression cassette fusion protein results in cell death. However, the cleavage of the target DNA sequence by the homing endonuclease, before arabinose-mediated induction of mutant barnase expression, can eliminate the plasmid encoding mutant barnase, resulting in cell survival. Another system is described in U.S. application 20070042404 and involves the same basic principle of linking an endonuclease cleavage event with cell survival. When an endonuclease cleaves its cognate endonuclease recognition site located on a vector containing a toxic reporter protein, the vector is degraded and the cell survives because the toxic reporter protein cannot be produced. The cell also expresses a transporter protein that facilitates transport of a regulatory molecule used to induce expression of the toxic reporter protein. Transport protein expression results in a decrease in background cell growth attributed to cells that survive in the absence of plasmid degradation and the presence of a small molecule. Selected engineered nucleases are than screened in vitro and selected for their ability to bind target DNA sequences and to cleave the target DNA as described above. In one embodiment, variants that bind the target DNA sequence with high affinity and specificity and show a specific cleavage of the target sequences are selected.

Applications

In some aspects, the invention relates to engineered endonucleases that are useful in the assembly of DNA from smaller nucleic acid fragments, wherein the fragments with compatible or matching overhangs are annealed and ligated. For example, one of the limitation of type IIS restriction enzymes is the relative abundance of their recognition sites in the target DNA to be assembled. While it is possible to identify restriction endonucleases that do not cut within a typical gene sized fragment of approximatively 1 kb, significantly longer fragments (e.g., large sections of chromosomes, eukaryotic regulatory elements, operons, etc., or any combination thereof) are likely to contain a majority of the endonucleases recognizing sequences of four to eight bps.

In some embodiments, engineered nucleases can be used to process nucleic acid substrates to generate specific nucleic acid fragments for assembly into larger predetermined nucleic acid products. The nucleic acid substrates may be obtained from oligonucleotide assembly reactions, other assembly steps, amplification reactions, clones, or any other suitable source as the invention is not limited in this respect. In some embodiments, an engineered nuclease can be used in a nucleic acid assembly procedure that includes a series of assembly steps. Engineered nucleases can be used at one or more stages to process a nucleic acid product from a first assembly step for subsequent assembly in a second step that produces a larger nucleic acid product. Aspects of the invention can be useful to generate fragments with termini that include specific single strand overhangs (e.g., 3' or 5' overhangs) for subsequent ligation or cloning. In some embodiments, the overhangs include only sequences of a target nucleic acid being assembled and do not include sequences of a flanking region that contains the nucleic acid motif recognized by the binding domain of the engineered nuclease.

In one aspect of the invention, synthetic nucleic acids of at least 500 bps, or at least 1, 5, 10, 15, 20, 30, 40, 50, 60, 70, 80, 90, 100 kb or at least about 1 mb, or longer are assembled. As one skilled in art will appreciate the most common type of restriction enzyme (such as 4-6 bp cuters) will cut every about 1 kb generate a multitude of DNA fragments with identical overhangs, leading to random assembly of the fragments. Use of an engineered endonuclease of the invention comprising a catalytic domain cutting outside the recognition site produces cleavage sites adjacent to the DNA recognition site. Thus, each overhang would have a sequence specific to a part of the DNA distinct from the other sites and association of the specifically complementary cohesive ends will cause the segments to associate in the proper order. In the above approach, the length of the recognition sequence of the endonuclease allows the prediction of the number of fragments produced. For example, an enzyme recognizing a 8 bp motif will typically cut every 65 kb DNA, an enzyme recognizing a 10 bp will cut once every 1 mb and an enzyme recognizing a 14 bp will cut once every 268 mb. Desirably, one skilled in the art would use an enzyme that recognizes a DNA binding motif which length would be sufficient so that the DNA recognition sites are statistically unlikely to be in the target nucleic acid of the size that is being synthesized and therefore unlikely to be present in the pool of polynucleotides or nucleic acids being assembled. In an exemplary embodiment, an engineered nuclease recognizing a 8 bp recognition motif is used for the assembly of a 50 kb nucleic acid, an engineered nuclease recognizing a 10 bp recognition motif is used for the assembly of a 1 mb nucleic acid, and an engineered nuclease recognizing a 14 bp is used for the assembly of 200 mb nucleic acid.

The necessary restriction sites can be specifically included in the design of the sequence or the random distribution of the restriction sites within a desired sequence can be utilized. In another embodiment, two different engineered nucleases recognizing two different recognition motifs can be used to allow two fragments to be joined together in a desired order. Nucleic acid sequences may be designed and synthesized to contain recognition and cleavage sites for one or more restriction endonucleases at sites that would facilitate joining in a specified order.

Accordingly, aspects of the invention relate to an engineered chimeric endonuclease, comprising a nucleic acid binding domain of a first endonuclease wherein the nucleic acid domain binds a recognition motif on a target nucleic acid and wherein a catalytic domain of the first endonuclease is inactive; and a nucleic acid cleavage domain of a second endonuclease wherein the nucleic acid cleavage domain cleaves said target nucleic acid at a cleavage position outside of said recognition motif, wherein the recognition motif comprises at least 5 (and preferably at least 6, at least 7, or at least 8) nucleotides. In some embodiments, the nucleic acid binding domain is linked to the nucleic acid cleavage domain via a peptide linker. Accordingly, in some embodiments, the chimeric endonuclease comprises a nucleic acid binding domain wherein the nucleic acid domain binds a recognition motif on a target nucleic acid; and a nucleic acid cleavage domain of an endonuclease wherein the nucleic acid cleavage domain cleaves said target nucleic acid at a cleavage position outside of said recognition motif, wherein the recognition motif comprises at least 8 nucleotides and wherein the nucleic acid binding domain is linked to the nucleic acid cleavage domain via a peptide linker.

In some embodiments, the cleavage domain comprises at least one catalytic domain of a Type IIS endonuclease. In some embodiments, the cleavage domain comprises two identical catalytic domains or two different catalytic domains, wherein the cleavage domain comprises a catalytic domain from a BstF5 I, BtsC I, BsrD I, Bts I, Alw I, Bcc I, BsmA I, Ear I, Mly I, Ple I, Bmr I, Bsa I, BsmB I, Fau I, Mnl I, Sap I, Bbs I, BciV I, Hph I, Mbo II, BfuA I, BspCN I, BspM I, SfaN I, Hga I, BseR I, Bbv I, Eci I, Fok I, BceA I, BsmF I, BtgZ I, BpuE I, Bsg I, Mme I, BseG I, Bse3D I, BseM I, AclW I, Alw26 I, Bst6 I, BstMA I, Eam1104 I, Ksp632 I, Pps I, Sch I, Bfi I, Bso31 I, BspTN I, Eco31 I, Esp3 I, Smu I, Bfu I, Bpi I, BpuA I, BstV2 I, AsuHP I, Acc36 I, Lwe I, Aar I, BseM II, TspDT I, TspGW I, BseX I, BstV1 I, Eco57 I, Eco57M I, Gsu I, or a Bcg I Type IIS endonuclease. In some embodiments, the cleavage domain comprises at least one catalytic domain of a Fok I restriction endonuclease. In some embodiments, the cleavage domain comprises the at least one catalytic domain of a FokI restriction endonuclease associated with at least one portion of a DNA recognition subdomain of the FokI restriction endonuclease. In some embodiments, the cleavage domain comprises the at least one catalytic domain of a FokI endonuclease associated with a variant of a D1D2D3 subdomain of a FokI DNA recognition domain wherein the variant D1D2D3 subdomain does not bind said target DNA. In some embodiments, the D1 subdomain is prepared by introducing an amino acid substitution in one or more positions selected from the group comprising Q12S, N13S, R79Q, and Q95S. In some embodiments, the cleavage domain comprises the at least one catalytic domain of FokI endonuclease associated with a variant of a D2D3 subdomain of a FokI DNA recognition domain wherein the variant D2D3 subdomain does not bind to said target DNA. In some embodiments, the D2 subdomain is prepared by introducing an amino acid substitution in one or more positions selected from the group comprising E220N, K225S, R228Q. In some embodiments, the D3 subdomain is prepared by introducing mutations L184N, F192Y, I230T, W233K, L234S, L237E, L239N, V274T and V287T.

In some aspects, an engineered endonuclease has nanomolar or pico-molar affinity for the target nucleic acid. However, higher or lower affinities also may be used (e.g., micromolar, mmolar, or femptomolar, etc.)

In some embodiments, the peptide linker is 10 or more amino acids in length, 14 or more amino acids in length, 20 or more amino acids in length, 22 or more amino acids in length, 30 or more amino acids in length, or 40 or more amino acids in length. In some embodiments, the peptide linker comprises about 70% G, 20% S, 5% D and 5% N. In some embodiments, the peptide linker comprises about 30% G, 20% S, 30% D, 5% R, 5% K, 5% N, and 5% P. In some embodiments, the peptide linker comprises one of the following amino acid sequences:

```
                                              SEQ ID NO: 49
QFVIPNRGVTKQLVK (natural Fold linker), SEQ ID NO: 35
Link10s  GGSGGDGSGG, SEQ ID NO: 36
Link10d  GGDSRDSDGG, SEQ ID NO: 37
Link14s  GGSGGSGDGGGSGG, SEQ ID NO: 38
Link14d  GGDSRDPSDKSDGG, SEQ ID NO: 39
Link20s  GGGSGGSDGSGNGGSGSGGG, SEQ ID NO: 40
Link20d  GGSGDRDDSDPSDKNDGSGG, SEQ ID NO: 41
Link22s  GGGSGGSGDGSGNGGSSGSGGG, SEQ ID NO: 42
Link22d  GGSGDRDGDSDPSDKNDDGSGG, SEQ ID NO: 27
Link25s  GGSGGGSGDGSGNGGSGGDSGGSGG, SEQ ID NO: 28
Link25d  GGSGDRDGSDSDRPDSDKNDDGSGG, SEQ ID NO: 43
Link30s  GGSGGGSGDGSGGGSGGNSGGDGSGGSGG,
or SEQ ID NO: 44
Link30d  GGSGDGRDGSDNSGDDRPDSGDKNDDGSGG.

SEQ ID NO: 29
Link40s
GGSGGSGGNGGGSGGDGSGRSGGNGGGDGGSGGGSGSGG,

SEQ ID NO: 30
Link40d
GGSGDGDSKDDSDPRDGDNSGGRDNPDSDGSGSKDDGSGG,
```

-continued

```
                                              SEQ ID NO: 31
Link75s
GGSGGDSGPSGGGNGGSGRDGGGSNGGSRGSGGDSGPSGGGNGGSGGSGK DGGGNGGSGGKDSGGNGGSGGGSGG,
or SEQ ID NO: 32
Link75d
GGSGDGDSKDGSDPDNGDSRDGGNPGDGSGRDGDGSGDNGDGPSRSDSKS

SDDSDKNPDGDSGDRSDGDKDGSGG.
```

In some embodiments, the spacer polypeptide has the amino acid composition (S design) 70% G, 20% S, 5% D, and 5% N, or (D design) 30% G, 20% S, 30% D, 5% R, 5% K, 5% N, and 5% P.

In some aspects, a nucleic acid cleavage domain specifically cleaves DNA (e.g., specifically cleaves double-stranded DNA).

In some embodiments, two catalytic domains are covalently linked to the binding domain via a linker. In some embodiments, the linker is a peptide linker. In some embodiments, the peptide linker is at least 10 amino acids long.

In some embodiments, the nucleic acid binding domain is a DNA binding domain (e.g., a double-stranded DNA binding domain). In some embodiments, the nucleic acid binding domain specifically recognizes a recognition motif that is between 10 and 20 bases long, between 20 and 40 bases long, between 40 and 100 bases long, or longer.

In some embodiments, the nucleic acid binding domain comprises a meganuclease nucleic acid binding domain. In some embodiments, a meganuclease catalytic activity is inactivated by modifying the nucleotide sequence coding for selected amino acid residues in a catalytic site generating an inactive meganuclease variant. In some embodiments, the meganuclease variant is an inactive intron-coding homing endonuclease (e.g., a "LAGLI-DADG" endonuclease, a "His-Cys" Box endonuclease, "GIY-YIG" endonuclease, and/or a "HNH" endonuclease. In some embodiments, the nucleic acid binding domain comprises an inactive I-SceI, I-SceII, I-DmoI, I-CreI, I-CeuI, PI-SceI, I-Ppo, I-TevI, I-TevII, I-TevIII, I-CeuI, or PspI domain. In some embodiments, the inactive variant I-Sce endonuclease comprises an N at position 44 and an A at position 145. In some embodiments, the inactive variant I-Sce endonuclease comprises an A at position 44 and an A at position 145. In some embodiments, the inactive variant I-Cre endonuclease comprises an N at position 20 and an A at position 47.

Aspects of the invention relate to nucleic acids encoding one or more of the engineered endonucleases of the invention (e.g., nucleic acids encoding chimeric fusion proteins of the invention).

Other aspects of the invention relate to a plurality of nucleic acid sequences for assembly of a nucleic acid construct having a predetermined sequence, the plurality of nucleic acid sequences comprising a recognition motif of at least 5 (e.g., at least 6, at least 7, at least 8) nucleotides long for an engineered chimeric nuclease, wherein the engineered chimeric nuclease comprised a binding domain that specifically binds the recognition motif on said plurality of nucleic acid sequences and a nucleic acid cleavage domain that cleaves said nucleic acid sequences at a cleavage position outside said recognition motif.

Other aspects of the invention relate to a method for assembling a nucleic acid construct having a predetermined sequence, by providing a plurality of nucleic acid sequences comprising a recognition motif of at least 5 (e.g., at least 6, at least 7, at least 8) nucleotides long for an engineered chimeric nuclease; generating the engineered chimeric nuclease comprising a nucleic acid domain linked to a nucleic acid cleavage domain from a nuclease via a peptide linker, wherein the nucleic acid domain specifically binds the recognition motif on the nucleic acid sequences and wherein the nucleic acid cleavage domain cleaves said nucleic acid sequences at a cleavage position outside said recognition motif; cleaving said nucleic acid sequences with the engineered chimeric nuclease; and assembling the cleaved nucleic acid sequences to form the nucleic acid construct.

In some embodiments, the nucleic acid sequences comprise two distinct recognition motifs for two distinct engineered nucleases. In some embodiments, the nucleic acids comprise a recognition motif for a chimeric engineered nuclease wherein the nucleic acid domain is from an endonuclease. In some embodiments, the nucleic acids comprise a recognition motif for a chimeric engineered nuclease wherein the nucleic acid domain is from a DNA binding protein. In some embodiments, the DNA binding domain is selected from zinc fingers, viral replication proteins, α-helical DNA binding proteins, DNA binding moities of gene transcription factors, repressors, oncogenes, nuclear hormone receptors, TATA binding proteins, leucine zipper type proteins, beta-sheet motif proteins, helix-turn-helix motif proteins, POU domains, or any naturally occurring sequence specific DNA binding proteins recognizing at least 5 (e.g., at least 6, at least 7, at least 8) nucleotides.

In some embodiments of the methods or plurality of nucleic acids, the predetermined sequence is about 50 kb in length or about 100 kb in length. In some embodiments, the predetermined sequence is about 50 kb in length and the recognition motif is at least 5 (e.g., at least 6, at least 7, at least 8, or at least 9) nucleotides long. In some embodiments, the predetermined sequence is about 1 mb in length. In some embodiments, the predetermined sequence is about 1 mb in length and the recognition motif is at least 10 nucleotides long. In some embodiments, the binding domain of the engineered nuclease is linked to the cleavage domain via a peptide linker. In some embodiments of the methods or plurality of nucleic acids, the nucleic acid sequences comprise two distinct recognition motifs for two distinct engineered nucleases. In some embodiments, the nucleic acid binding domain is from an endonuclease or a DNA binding protein. In some embodiments, a DNA binding domain is selected from zinc fingers, viral replication proteins, α-helical DNA binding proteins, DNA binding moities of gene transcription factors, repressors, oncogenes, nuclear hormone receptors, TATA binding proteins, leucine zipper type proteins, beta-sheet motif proteins, helix-turn-helix motif proteins, POU domains, replication-terminator proteins, or any naturally occurring sequence specific DNA binding proteins recognizing at least 5 (e.g., at least 6, at least 7, or at least 8) nucleotides.

Accordingly, aspects of the invention relate to isolated chimeric enzymes or domains or portions thereof, nucleic acids (e.g., cassettes, vectors, linear nucleic acids, plasmids, with or without regulatory sequences such as promoters, with or without selectable markers, etc., or any combination thereof) encoding full length chimeric enzymes or domains or portions thereof, host cells containing the nucleic acids, kits for expressing and isolating the enzymes, kits for assembling nucleic acids using the enzymes, and other aspects of the invention described herein.

EXAMPLES

Example 1

Modeling and Design of Hybrid I-SceI-FokI Enzymes

Structural models were built using the Schrödinger software suite (Schrödinger, LLC). The FokI dimer (2FOK, Wah et al, 1998) was structurally aligned to the DNA-bound BamHI dimer (1BHM; Newman et al., 1995, Science, 269: 656-663) using the Protein Structure Alignment function on residues 418-579 of FokI and residues 1-180 of BamHI, leading to the model of a dimer of FokI catalytic domains bound to DNA.

The FokI dimer was positioned on the DNA downstream of the FokI recognition site (1FOK, Wah et al., 1997) by aligning the DNA backbone adjacent to the original BamHI cleavage site in the dimer complex to the known 9/13 site of FokI cleavage (1FOK: B913-B920, C922-C929; 1BHM: C1-C8, D5-D12). The wild-type FokI linker, previously defined as residues 373-387, was modeled as follows: The backbone dihedral angles of residues 382-387 were modified to a-helical, and the backbone dihedral angles of residues 376-382 were adjusted to create a new backbone turn to position the 382-387 helix for continuation into helix residues 388-399 of the catalytic domain. Next, the Prime Minimization function was used with residues 375-389 to find a structurally similar, low energy conformation. Separately, the Prime Refine Loops function was applied to residues 375-389 to generate a series of low-energy loop conformations. Alternate FokI models with the catalytic dimer at different positions downstream of the recognition site were generated by aligning the same 1BHM DNA base pairs to shifted base pairs of 1FOK. To model the hybrid enzymes, similar alignments were used to position the FokI dimer on DNA downstream of I-SceI (1R7M, Moure et al., 2003). Distances between domain termini were measured in Maestro, and alternative alignments generated using a different amount of DNA backbone in the vicinity of the cleavage site provided estimates of sensitivity.

Results:

Since no structural information is available on FokI bound to and cleaving DNA, the structural mechanism of the wild-type FokI type IIS endonuclease was modelled following the approach previously described by Wah et al., using available structures of monomeric FokI bound to DNA in an inactive, sequestered conformation, dimeric FokI without DNA, and BamHI bound to DNA. First the DNA-free FokI dimer structure was aligned to a crystal structure of the complex of BamHI and DNA (FIG. 5($a$)). In this model, the three catalytic residues of each FokI monomer are in a similar location to their homologous BamHI catalytic residue, with the FokI catalytic residues positioned over DNA-backbone phosphates to produce the four-base overhangs found in FokI digestion products. Next, the DNA backbones from the model of the FokI catalytic domain dimer on DNA and from a crystal structure of the FokI monomer bound to DNA were aligned so that the cleavage domains were positioned at the FokI native cut sites, nine and thirteen bases downstream of the recognition site (9/13). The cut thirteen bases from the recognition domain is made by the FokI molecule whose DNA-binding domain was modeled to bind the recognition domain, whereas the cut nine bases from the recognition domain is made by the second FokI catalytic domain, which is positioned through noncovalent interactions between the two catalytic domains. Modeling of the fifteen-residue native linker that connects the C-terminus of the recognition domain to the N-terminus of the closer of the two catalytic domains produced several low-energy linker conformations. In the linker models, residues 373 to 377 adopt approximately the same conformation as in the initial sequestered state, residues 378 to 382 adopt a new turn, and residues 383 to 387 connect to and extend the a-helix at the N-terminus of the catalytic domain.

An attempt to reposition the FokI cleavage domains even a single base pair away from its 9/13 cleavage site resulted in clashes or large changes in distance between the C-terminal end of the recognition domain and the N-terminus of the FokI cleavage domains. When the cleavage domain was moved one or more base pairs further from the recognition domain, the distance between the two domains became too large to be spanned by the native FokI linker without at least breaking the intramolecular contacts at residues 373 to 377, or stretching into an extended conformation. Conversely, positioning the FokI cleavage domains on DNA closer to the recognition site resulted in steric clashes between the recognition and catalytic domains (Table 1(a)).

of each monomer of the FokI cleavage domain dimer was measured (Table 1(b)), and linkers were designed to span this distance. The N-terminus of at least one of the FokI catalytic domains was found to be between approximately 20 Å and 35 Å of the C-terminus of I-SceI when the cleavage domain dimer is positioned to cut 1/5, 2/6, or 3/7 nucleotides downstream of the I-SceI recognition site. Theory for the end-to-end distance of flexible polypeptides as a function of the number of residues predicts that this distance can be spanned by linkers in the range of 10-20 residues. A shorter, ten-residue linker would be expected to favor the 1/5 position, which is closer to the I-SceI recognition sequence; conversely, a longer, 20-residue linker would be expected to favor the 2/6 and 3/7 positions, which are further from the I-SceI recognition sequence. Four novel linker sequences were chosen, two of which are ten amino-acid residues in length, and two of which are 20 residues in length. These designed linkers are rich in glycine, polar, and charged amino-acid residues, and contain few residues with preference for a-helical or b-strand secondary structure (William et al. 1987, Biochim.

TABLE 1

Modeling the FokI catalytic dimer at different positions on DNA relative to the FokI and I-SceI recognition domains.

| Position of catalytic domains on DNA[a] | # catalytic-domain residues that clash with the recognition domain | Distance from C-terminus of recognition domain to N-terminus of each catalytic domain (Å) | |
|---|---|---|---|
| | | Upstream catalytic domain | Downstream catalytic domain |
| (a) Downstream of FokI recognition domain (native FokI) | | | |
| 7/11 | 20 | 70 | 39 |
| 8/12 | 3 | 70 | 23 |
| 9/13[b] | 0 | 67 | 24 |
| 10/14 | 0 | 59 | 33 |
| 11/15 | 0 | 53 | 48 |
| (b) Downstream of I-SceI recognition domain (hybrid endonuclease) | | | |
| 0/4 | 3 | 45 | 15 |
| 1/5[c] | 0 | 41 | 22 |
| 2/6[c] | 0 | 34 | 34 |
| 3/7[c] | 0 | 28-36 | 38-44 |
| 4/8 | 0 | 37 | 46 |
| 5/9 | 0 | 43 | 50 |

[a]Defined by predicted number of nucleotides between 3' end of recognition site and site of DNA cleavage.
[b]Model consistent with observed wild-type FokI cleavage. The fifteen-residue native linker connects the C-terminus of the DNA-bound recognition domain to the N-terminus of the downstream catalytic domain, 24 Å away.
[c]Models used to design linkers for hybrid I-SceI/FokI endonucleases, based on the absence of catalytic-domain clashes and at least one distance between domain termini shorter than 35 Å.

Hybrid I-SceI/FokI enzymes were designed by first modeling the FokI catalytic domain dimer on DNA at different positions downstream of the I-SceI homing endonuclease. The distance from the C-terminus of I-SceI to the N-terminus Biophys. Acta 916:200-204; Wilmot et al. J. Mol. Biol. 203: 221-231) (Table 2). In addition to the four designed linkers, the linker from wild-type FokI, FokL, which is fifteen residues long, was tested.

TABLE 2

The linkers used in the hybrid I-SceI/FokI enzymes and a summary of experimentally determined enzyme cleavage properties.[a]

| | Linker sequence | Source | # aa's | Linker name | Enzyme name | Cleavage at I-Sce-I recognition site | Non-specific cleavage | Overhang |
|---|---|---|---|---|---|---|---|---|
| SEQ ID NO: 33 | QFVIPNRGVTKQLVK | Fok1 | 15 | FokL | CdnDI | Yes | None | 2/7 |
| SEQ ID NO: 40 | GGSGDRDDSDPSDKNDGSGG | Design | 20 | 20D | CdnDII | Yes | Minor | 2/7 |
| SEQ ID NO: 39 | GGGSGGSDGSGNGGSGSGGG | Design | 20 | 20S | | Yes | Minor | 2/7 |

TABLE 2-continued

The linkers used in the hybrid I-SceI/FokI enzymes and a summary of
experimentally determined enzyme cleavage properties.[a]

| Linker sequence | Source | # aa's | Linker name | Enzyme name | Cleavage at I-Sce-I recognition site | Non-specific cleavage | Over-hang |
|---|---|---|---|---|---|---|---|
| SEQ ID NO: 36 GGDSRDSDGG | Design | 10 | 10D | | Yes | Moderate | 1/7 |
| SEQ ID NO: 35 GGSGGDGSGG | Design | 10 | 10S | | Yes | Extensive | 1/5 |

[a]The sequence of each full-length hybrid protein was: [SEQ ID NO: 45 MGHHHHHHENLYFQGSGS][Residues 3-225 of I-SceI as in pdb 1R7M (Moure CM, J Mol Biol. 2003 Dec. 5; 334(4): 685-95)][Linker as defined above][Residues 388-579 of FokI as in pdbs 1FOK (Wah DA, et al., Nature. 1997 Jul. 3; 388(6637): 97-100] and 2FOK (Wah DA, et al., Proc Natl Acad Sci U S A. 1998 Sep. 1; 95(18): 10564-9)].

Example 2

Construction of Active-Site Mutants of I-SceI and of Hybrid Endonucleases

Figure 5:
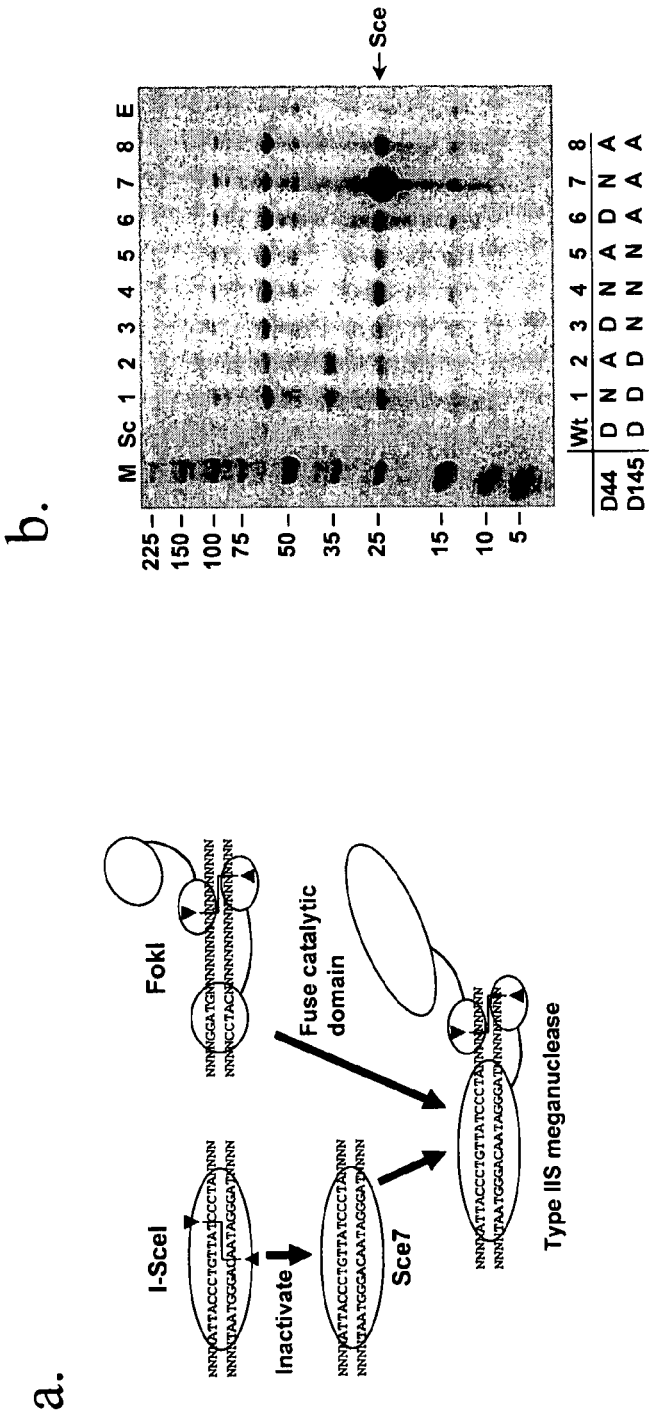
FIG. 5 illustrates a non limiting embodiment of an engineered endonuclease comprising a non cleaving mutant of the homing endonuclease I-SceI linked to the DNA cleavage domain of the type IIS FokI.

All DNA constructs used in this study were assembled from synthetic oligonucleotides using PCR- and ligation-based DNA-assembly methods and error-correction technology. The eight I-SceI variant genes constructed in addition to the wild-type I-SceI gene contained all possible single and double mutations of Asp 44 and Asp 145 to either alanine or asparagine (FIG. 5). Genes for the hybrid endonucleases were assembled from an upstream fragment of DNA encoding the inactive, DNA-binding I-SceI variant Sce7 (D44N, D145A); a middle fragment of DNA encoding a 10-, 15-, or 20-residue linker; and a downstream fragment of DNA encoding the wild-type catalytic domain of FokI. The protein sequences of the hybrid endonucleases described in this report are detailed in the footnote of Table 2. Each I-SceI variant gene and hybrid-endonuclease gene was cloned between the NcoI and XhoI sites of vector pBAD-His (A) (Invitrogen, Carlsbad, Calif.), transformed into Top10 OneShot cells (Invitrogen), and plated onto LB agar with 100 mg/mL of carbenicillin (LB/carb).

All eight single and double mutants were found to be expressed in *E. coli* at a higher level than was wild-type I-SceI, with mutant Sce7 (D44N, D145A) yielding the highest amount of soluble protein (FIG. 5b). Purified Sce7 does not cut linear, double-stranded DNA containing the native I-SceI recognition site (FIG. 5a), but it does bind to that DNA sequence (FIG. 6a,b,c). The binding affinities for the I-SceI recognition sites were determined using a gel-shift assay and are depicted in Table 3.

TABLE 3

Binding affinities for the I-SceI recognition sites

| Protein | Binding affinity (nM) |
|---|---|
| I-SceI | 62 ± 16 |
| Sce7 | 13 ± 2 |
| CdnDI | 19 ± 6 |
| CdnDII | 5.0 ± 1.2 |

Example 3

Screen for High Expression Level of I-SceI Mutant Proteins in *E. coli*

Figure 6:
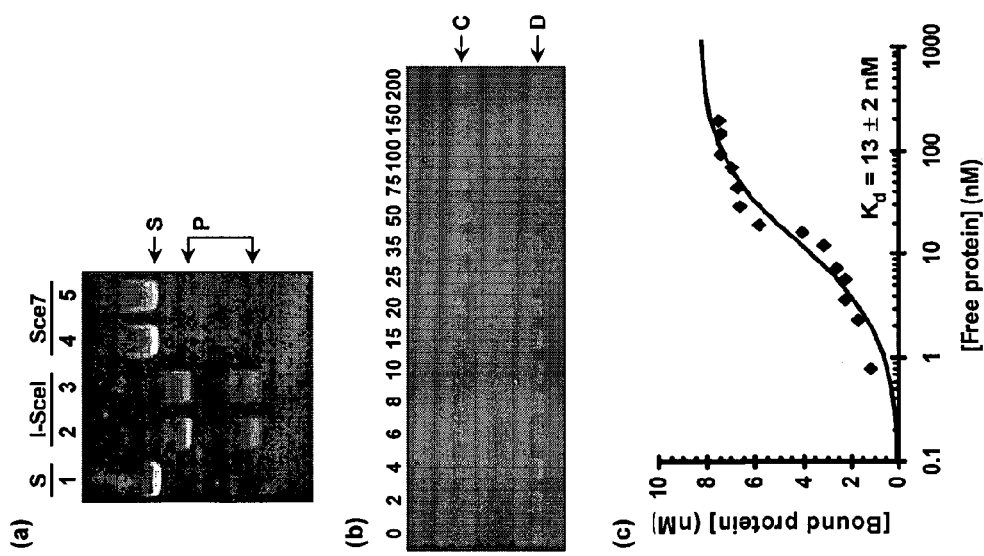
FIG. 6 illustrates a non limiting embodiment of wild type I-SceI and non cleaving mutant I-SceI (Sce7)

To test the expression level of each I-SceI mutant, individual colonies were used to inoculate 1 mL of LB/carb, and grown overnight, with shaking, at 37° C. Ninety mL of the overnight culture was added to 3 mL of fresh LB, and grown for 2.5 to 3 hours, to mid-log phase, at 37° C. Arabinose was added to each culture to 0.02%, and the cultures were incubated for three more hours at 37° C. The cell pellets were recovered by centrifugation (10 minutes at 3,220 g, 4° C.), stored frozen at −20° C., then thawed on ice and lysed in 350 iL of 50 mM sodium phosphate, pH 7.0, 0.5M NaCl, 50 mM MgCl2, 0.5 mg/mL lysozyme, 0.05 mg/mL DNaseI, and 1' EDTA-free COMPLETE protease inhibitor cocktail (Roche, Indianapolis, Ind.). Cellular debris was removed by centrifugation for 2 minutes at 16,000 g, 4° C. Thirty mL of 50% slurry of TALON Superflow Metal Affinity Resin (Clontech, Mountain View, Calif.), pre-equilibrated with 50 mM sodium phosphate, pH 7.0, 0.5M NaCl, and 50 mM MgCl2, were added to each, and the mixtures were rocked for an hour at 4° C. Each resin was washed three times with 400 iL of ice-cold PBS, pH 7.4, then resuspended in 25 mL of PBS. The resuspended resin was combined with reducing SDS-PAGE buffer, boiled at 99° C. for 5 minutes, separated on 4-12% Bis/Tris gradient gels in MES-based buffer (Invitrogen), and detected with GelCode Blue (Pierce, Rockford, Ill.) (FIG. 6).

Example 4

Purification of I-SceI Variant Sce7 and Hybrid Endonucleases

A single colony harboring the sequence-verified gene of interest was grown in 100 mL LB/carb overnight, with shaking, at 37° C. The overnight culture of Sce7 was diluted 1/33 into the final volume of two liters of fresh LB/carb, grown in shaker flasks for 2.5 to 3 hours, at 37° C., to mid-log phase, induced by adding arabinose to 0.02%, grown for three more hours at 37° C., and harvested by centrifugation for 30 minutes at 4,785×g, 4° C. In contrast, hybrid endonucleases were expressed in four to six liters of LB/carb at 25° C., for 16-18 hours. The cell pellets were stored at −80° C., then thawed at 4° C. in 1/50 of the original culture volume of 10 mM HEPES, pH 8.0, 1 M NaCl, 1 mM DTT, 25 mM imidazole, 1' EDTA-free COMPLETE protease inhibitor cocktail, and 120 mg/ml lysozyme. Lysis buffer for purification of hybrid endonucleases also contained 1 mM PMSF. The lysate was sonicated, then clarified by centrifugation for 20 minutes at 6,000 g, 4° C., followed by filtration of the supernatant through a 0.45 mm filter. All further purification steps were performed at 4° C.

The clarified lysate was loaded onto a 1 mL HisTrap column (GE Healthcare, Piscataway, N.J.) pre-equilibrated with 10 mM HEPES, pH 8.0, 1 M NaCl, 25 mM imidazole, and 1 mM DTT on the AKTA Purifier chromatography system (GE Healthcare), at the flow rate of 1 mL/minute. The column was washed with 20 column volumes of the equilibration buffer, then eluted with a linear gradient of 25 to 100 mM imidazole in equilibration buffer over 30 column volumes. The fractions containing eluted protein were pooled, concentrated using Amicon (Houston, Tex.) Ultra-15 centrifugal concentrators (10 kD MWCO) to between approximately 1 mL, and filtered through a 0.2 mm filter. The partially purified protein was loaded onto a HiLoad Superdex 200 16/60 column (GE Healthcare) pre-equilibrated with 20 mM HEPES, pH 8.0, 0.5 M NaCl, 1 mM DTT, 0.1 mM EDTA, and 5% glycerol on the AKTA Purifier. The size-exclusion chromatography step was performed at 0.5 mL/minute. Fractions eluted from the column at the volume corresponding to the expected molecular weight (approximately 38 kD for the Sce7 mutant and 52 kD for the hybrid endonucleases) were pooled, concentrated using Amicon Ultra-4 centrifugal concentrators (10 kD MWCO) at 2,000 g, 4° C. (to 160 ig/mL for Sce7 and between to between 100 and 300 ig/mL for the hybrid endonucleases, and stored at −20° C. in 10 mM HEPES, pH 8.0, 0.25 M NaCl, 0.5 mM DTT, 0.05 mM EDTA, and 50% glycerol.

Results:

The purified hybrid enzymes were tested in an in vitro DNA-cleavage assay. A plasmid containing a single copy of the I-SceI recognition sequence was linearized and incubated with hybrid enzyme under a range of reaction conditions, and then the substrate and cleaved DNA fragments were separated by agarose gel electrophoresis. The activity and specificity of the hybrid enzymes was found to be affected by both reaction conditions and the linker sequence (7). Under optimized reaction conditions (4-hour incubation with 50 nM CdnDI or 100 nM CdnDII in 20 mM Tris.HCl, pH 9.0, 25 mM NaCl, 10 mM MgCl2, 1 mM dithiothreitol, 0.1 mg/mL bovine serum albumin, and 2% glycerol, at 37° C. for CdnDI or 42° C. for CdnDII), the hybrid enzymes CdnDI and CdnDII each cut the linearized substrate at a single site to produce two DNA fragments of the expected length (FIG. 6). In addition to this pair of major products, a minor trace of additional DNA fragments indicative of non-specific cleavage was observed in the case of CdnDII. In contrast, the remaining hybrid enzymes produced additional DNA fragments under the conditions tested, indicative of cleavage at one or more alternate sites (Table 2). The addition of excess Sce7 protein blocked cleavage at the I-SceI recognition site, but did not block cleavage at other sites (FIG. 6).

Under their optimal cleavage conditions, both CdnDI and CdnDII cleaved supercoiled plasmid DNA that contained a single copy of the I-SceI recognition site.

Example 5

Cleavage from Hybrid Enzymes

DNA Cleavage Assay

To construct a DNA substrate for I-SceI and the hybrid endonucleases, two complementary oligonucleotides containing the I-SceI recognition site ([SEQ ID NO: 46] 5'-AAT-TCTGGTTCCGAAGCCTGTCCTG-CACGCTAGGGATAACAGGGTAATAATA TATGAATCCAAACTAGAGCGGGGCTCT-TGACGTTTGGCTCAAAACGTCGTGA GACAGTTTG-GTCAGTTGTAAATATCTAATATTCCAATG-3' and

[SEQ ID NO: 47] 5'-GATCCATTGGAATATTAGATATT-TACAACTGACCAAACTGTCTCACGACGTTT TGAGC-CAAACGTCAAGAGCCCCGCTCTAGTTTG-GATTCATATATTATTACCCT GTTATCCCTAGCGT GCAGGACAGGCTTCGGAACCAG-3'; the I-SceI recognition site is underlined) were annealed, phosphorylated, and ligated between the EcoRI and BamHI restriction sites of pUC19 (Invitrogen). The plasmid was propagated in and extracted from *E. coli* OneShot Top 10 (Invitrogen), linearized by cleavage with AlwNI (New England Biolabs, Ipswich, Mass.) and purified using standard isopropanol/acetate precipitation.

To observe cleavage of the linearized, purified pSCI substrate by the hybrid endonucleases, 400 ng of the plasmid DNA were incubated for four hours under different reaction conditions. For the hybrid endonuclease CdnDI, the optimal cleavage conditions were 50 nM endonuclease in 20 mM Tris.HCl, pH 9.0, 25 mM NaCl, 10 mM MgCl2, 1 mM dithiothreitol, 0.1 mg/mL bovine serum albumin, and 2% glycerol, at 37° C. For the hybrid endonuclease CdnDII, the optimal cleavage conditions were 100 nM endonuclease in 20 mM Tris.HCl, pH 9.0, 25 mM NaCl, 10 mM MgCl2, 1 mM dithiothreitol, 0.1 mg/mL bovine serum albumin, and 2% glycerol, at 42° C. After the incubation, the reaction mixture was separated on a 0.8% agarose E-gel (Invitrogen). The DNA bands were visualized with ultraviolet light and quantified by densitometry using an AlphaImager HP imager (AlphaInnotech, San Leandor, Calif.) and ImageJ software (http://rsb.info.nih.gov/ij/).

To test the ability of hybrid endonucleases to cleave supercoiled DNA, 400 ng of circular pSCI were digested with CdnDI or CdnDII under the optimized cleavage conditions listed above, and the products were separated on a 0.8% agarose E-gel (Invitrogen).

Determination of Dissociation Constants

The DNA reagent for determining the dissociation constants between I-SceI variant Sce7 or hybrid endonucleases and DNA was prepared by annealing two 80-base oligonucleotides,

[SEQ ID NO: 48]
5'-GAATTCTGGTTCCGAAGCCTGTCCTGCACGCTAGGGATAACAGGGTA

ATAATATATGAATCCAAACTAGAGCGGGGCTCT-3'
and

[SEQ ID NO: 49]
5'-AGAGCCCCGCTCTAGTTTGGATTCATATATTATTACCCTGTTATCCC

TAGCGTGCAGGACAGGCTTCGGAACCAGAATTC-3'
(the I-SceI recognition site is underlined).

To measure the dissociation constants, the binding protein of interest, at a range of concentrations between 2 and 400 nM, was incubated with 10 nM DNA substrate in 20 iL of 20 mM Tris.HCl, pH 9.0, 25 mM NaCl, 10 mM CaCl2, 1 mM DTT, 2% glycerol, and 0.1 mg/mL BSA, for 20 minutes at 37° C. (Sce7 and CdnDI) or 42° C. (CdnDII). Two iL of 10' loading buffer were added to each sample, and 10 iL of each mixture were loaded onto 6% polyacrylamide DNA retardation gels (Invitrogen), and run for 30 minutes at 175 V. The gels were stained with SYBR Gold (Invitrogen) and visualized with ultraviolet light. DNA-containing bands were quantified by densitometry as described above. Concentrations of bound and free protein were calculated from the input amount of DNA and from ratios of band intensities, and the data were fit using Origin software (Originlab, Northampton, Mass.) to the following equation:

[Bound protein]=[DNA]total'[Free protein]/(Kd+[Free protein])Determination of cleavage sites of hybrid endonucleases Linearized pSCI was cleaved by CdnDI or CdnDII hybrid endonucleases under optimal cleavage conditions listed above. The resulting 1,900- and 900-base-pair DNA fragments were separated on a 1.2% agarose gel, then extracted from the gel using a Gel Extraction Kit (Qiagen, Valencia, Calif.). The 1,900-base-pair fragment was sequenced using oligonucleotide primer (SEQ ID NO: 50) 5'-ATTCGCCATTCAGGCTGCGC-3', and the 900-base-pair fragment was sequenced using oligonucleotide primer (SEQ ID NO: 51) 5'-CACTTTATGCTTCCGGCTCG-3'. The end of each fragment was deduced from the point where sequencing data terminated.

Figure 7:
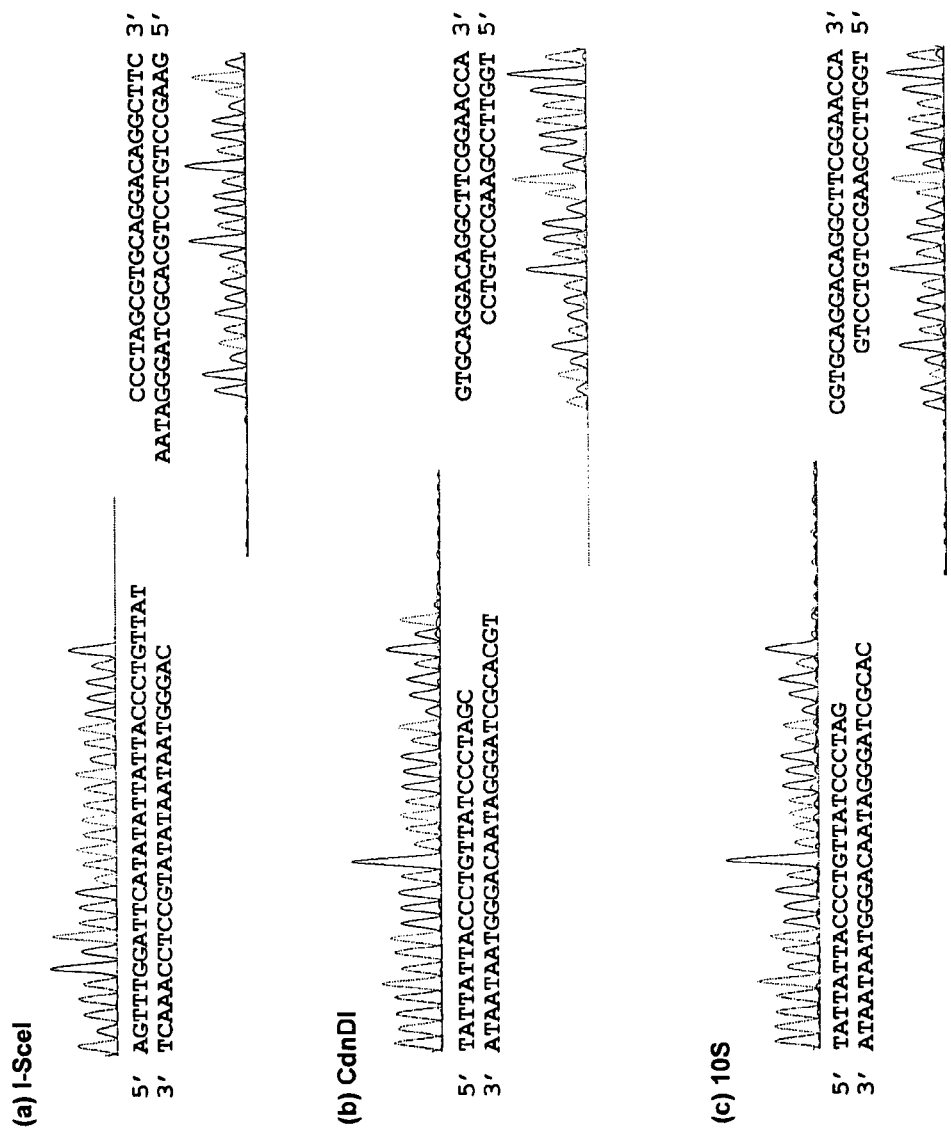
FIG. 7 illustrates a non-limiting embodiment of the determination of the cleavage site of the wild type, the engineered endonuclease CdnDI and an engineered endonuclease comprising the 10S linker (SEQ ID NO: 13 AGTTTGGAT-TCATATATTATTACCCTGTTAT; SEQ ID NO: 14 CAGGG-TAATAATATATGCCTCCAAACT; SEQ ID NO: 15 CCCTAGCGTGCAGGACAGGCTTC; SEQ ID NO: 16 GAAGCCTGTCCTGCACGCTAGGGATAA; SEQ ID NO: 17 TATTATTACCCTGTTATCCCTAGC; SEQ ID NO: 18 TGCACGCTAGGGATAACAGGGTAATAATA; SEQ ID NO: 19 GTGCAGGACAGGCTTCGGAACCA; SEQ ID NO: 20 TGGTTCCGAAGCCTGTCC; SEQ ID NO: 21 TAT-TATTACCCTGTTATCCCTAG; SEQ ID NO: 22 CACGCTAGGGATAACAGGGTAATAATA; SEQ ID NO: 23 CGTGCAGGACAGGCTTCGGAACCA; SEQ ID NO: 24 TGGTTCCGAAGCCTGTCCTG)
Figure 8:
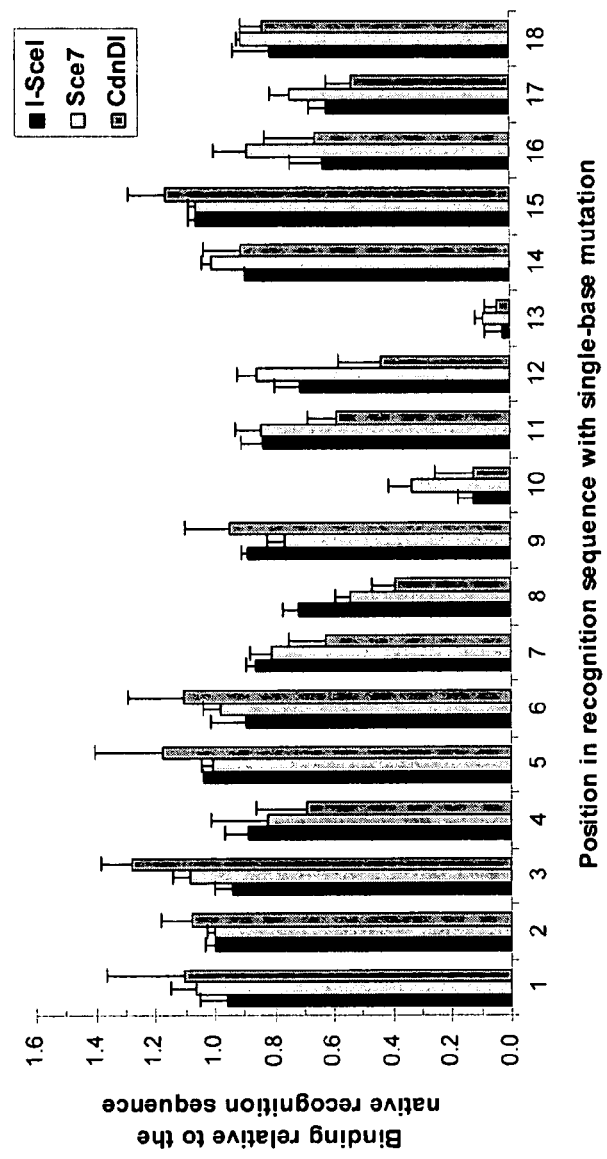
FIG. 8 illustrates a non-limiting embodiment of the binding specificity of wild type I-SceI, nuclease free Sce7, and engineered endonuclease CdnDI; and, FIG. 9 illustrates a non-limiting embodiment of the application of engineered endonucleases in assembly of DNA from smaller fragments.
Figure 9:
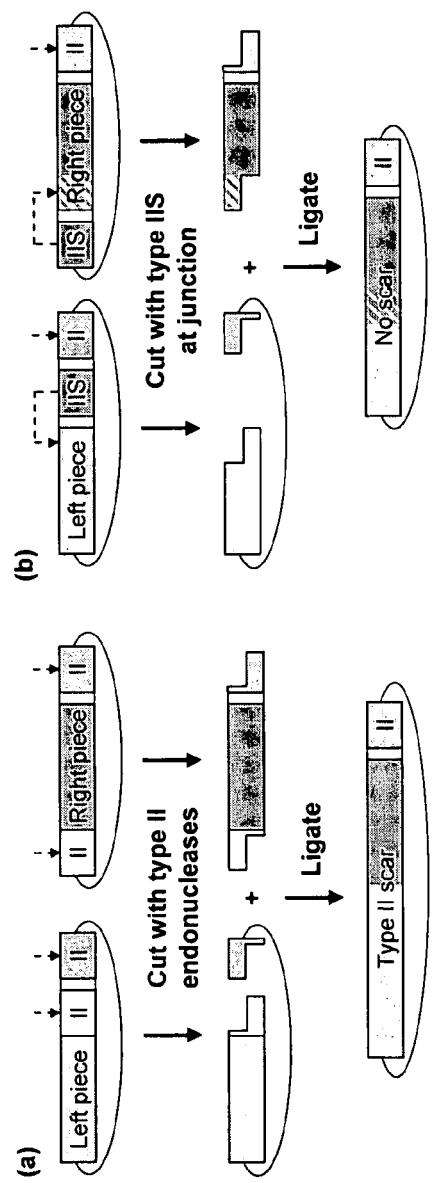

Results:

For wild-type I-SceI and hybrid enzymes CdnDI and CdnDII, the two products of DNA cleavage were extracted, purified, and sequenced in the direction toward the I-SceI recognition site to identify the exact location of the cleavage site for each enzyme (FIG. 7). For other hybrid enzymes, only the two products of DNA cleavage of the same length as those found for I-SceI were extracted, purified, and sequenced.

Sequencing traces for each enzyme tested dropped sharply at a specific site, which corresponded to the 5' end of that DNA cleavage product, indicating that DNA cleavage occurred predominantly at a single position (FIG. 7). For wild-type I-SceI, the sequences of the DNA products were consistent with the published cleavage site within the recognition site (Colleaux et al., 1988, PNAS 85:6022-6026. For all hybrid enzymes, the 5' end sequences of the two DNA products overlapped, indicating that these enzymes produce 5' overhangs. Occasionally, an additional "A" signal was observed after the final base in a fragment (e.g., FIG. 7(b), right-hand trace); this was attributed to the Taq polymerase used in the sequencing reactions (Clark, 1988, N.A.R. 16:9677-9686).

The sequences of DNA fragments produced by CdnDI, CdnDII, and the hybrid enzyme containing linker 20S all drop off at the exact same sites, which correspond to the ends of five-base, 5' overhangs, two and seven bases downstream of the recognition site (2/7). When tested on a substrate with a different DNA sequence downstream of the I-SceI recognition site, CdnDI still produced the same 5-base, 2/7 overhang. The hybrid enzyme containing linker 10S generates a 5', 1/5 overhang, and the hybrid enzyme containing linker 10D generates a 5', 1/7 overhang (Table 2).

Example 6

Affinity and Specificity of Hybrid Endonucleases for the I-SceI Recognition Site Eighteen double-stranded, 80-base-pair DNA reagents for evaluating endonuclease specificities were constructed as described above for determination of dissociation constants, except that each reagent contained a single base-pair substitution in the I-SceI recognition site. The following mutations were used in the different positions in the recognition site: 1: T'C, 2: A'C, 3: G'T, 4: G'T, 5: G'T, 6: A'C, 7: T'C, 8: A'C, 9: A'C, 10: C' T, 11: A'C, 12: G'T, 13: G'T, 14: G'T, 15: T'C, 16: A'C, 17: A'C, 18: T'C. The effect of each substitution on binding was assessed by following the procedure described above for determination of dissociation constants at 37° C., with the following modifications: For each of the eighteen mutated DNA reagents and for the original DNA reagent containing wild-type I-SceI recognition site, each protein was evaluated at a single concentration, which corresponded to approximately three times its Kd for the wild-type I-SceI recognition sequence (185 nM for I-SceI, 40 nM for Sce7, 50 nM for CdnDI). The percentage of each DNA substrate that bound to each protein was determined by densitometry. Each measurement was conducted three to four times. For each single-substitution substrate, the average percentage bound was normalized to the average percentage bound to the wild-type I-SceI recognition sequence.

Results:

The binding affinities of purified I-SceI, Sce7, CdnDI, and CdnDII for the I-SceI recognition site were estimated using a gel-retardation assay under conditions that inhibit DNA cleavage by the active enzymes. Each purified protein was incubated with double-stranded DNA that contained an I-SceI recognition site, and its apparent dissociation constant for the DNA was estimated from the dependence of fraction DNA bound on protein concentration. The Kd for I-SceI was estimated to be 62±16 nM, which is similar to its previously measured Km value of 34 nM at pH 9.5 (Montheilhet et al., 1990, N.A.R. 18:1407-1413). The inactive homing endonuclease mutant, Sce7, and hybrid enzymes CdnDI and CdnDII all bind substrate DNA three- to twelve-fold more tightly than does wild-type I-SceI.

The binding specificities of I-SceI, Sce7, and CdnDI for the native eighteen-base-pair I-SceI recognition sequence were investigated by comparing their binding to a series of near-native recognition sequences (FIG. 8) to their binding to the native recognition sequence. For the majority of single-base substitutions, all three proteins retain at least 50% of binding observed for the native binding sequence, as measured by the proportion of DNA bound to each protein. Mutations at positions ten and thirteen, however, have significant, deleterious effects on binding, with a similar effect on all three proteins. Overall, the specificity profile across all eighteen positions is essentially unchanged from the wild-type I-SceI to Sce7 and CdnDI.

Example 7

Assembly of DNA Fragments Generated by Hybrid Enzymes

```
                                                      SEQ ID NO: 52
TTCATGAGACGATCTCCTTCCTCTTGATGGCTGTAATAATAGCTCTAGGG

CGATGTTAAGACAACGGATTC

SEQ ID NO: 53
TTCAATATATTATTACCCTGTTATCCCTAGCGTGCAGGACAGGCTTCGGA

ACCGGAGACGTTGACAACATG
```

The hybrid endonucleases CdnDI and CdnDII were tested in ligation-based assembly. Two DNA fragments with complementary ends were ligated with a compatible acceptor vector and the DNA was transformed into E. coli. More than 80% of the colonies grown on selective plates were found to contain the correctly assembled insert for the donor fragments released by CdnDI and CdnDII, respectively.

Example 8

Expression and Purification of I-SceI and I-CreI Variants

The catalytic residues of the homing endonuclease SceI or I-CreI, were mutated by site directed mutagenesis to generate a DNA-binding protein devoided of catalytic activity. The mutated I-SceI and I-CreI (D20N, Q47A) enzymes were cloned behind an N-terminal 6× His tag and TEV cleavage site into a vector containing an arabinose promoter and an araC repressor protein (Invitrogen). The plasmids were transformed into *E. coli* (Top10, Invitrogen) and plated on LB/carbenicillin (carb) agar. Single colonies were picked and used to inoculate 100 ml LB/carb cultures. The cultures were grown overnight at 37° C. with shaking to saturation. The overnight cultures were diluted about 1:30 into 1 L fresh LB/carb and grown to mid-log phase (A600~0.6-0.8). Arabinose was added to the culture to a final concentration of 0.04%. The cultures were incubated at 37° C. for an additional 3 hours. The cells were harvested by spinning at 5000×g for 30 minutes at 4° C. The media was decanted and the cell pellets stored at −80° C.

Cell pellets were thawed on ice and resuspended in about ¹⁄₁₀th volume of Lysis Buffer (10 mM HEPES pH 8.0, 1M NaCl, 1 mM DTT, 25 mM Imidazole, 120 ug/ml lysozyme and Complete EDTA-free protease inhibitor cocktail (Roche, Ind.)). The lysate was incubated on ice for about 1 hour and then sonicated on ice (3×30 second bursts). The lysate was clarified by spinning at 6000×g for 30 minutes at 4° C.

A 1 ml HisTrap Fast Flow column (GE Healthcare cat#17-5319-01) was equilibrated in Loading Buffer (10 mM HEPES pH 8.0, 500 mM NaCl, 1 mM DTT, 25 mM Imidazole). The lysate was filtered through a 0.45U filter and loaded onto the equilibrated column. Unbound proteins were washed off the column by washing with 10 column volumes of Equilibration Buffer. The protein was eluted using a linear gradient from 0-100% Elution Buffer (10 mM HEPES pH 8.0, 1M NaCl, 1 mM DTT, 500 mM Imidazole). The eluted fractions were pooled and glycerol was added to 5% of the final volume. The sample was concentrated about 16 fold using an Amicon Ultra centrifugal concentration device A HiLoad Superdex 200 16/60 column (GE Healthcare) was equilibrated with Size Exclusion Chromatography (SEC) buffer (20 mM HEPES pH 8.0, 500 mM NaCl, 1 mM DTT, 5% glycerol, 0.1 mM EDTA). The sample was applied and the column was run at 1 ml/minute. The major peak was the monomeric protein of interest and it was pooled and concentrated about 10 fold as described above. The protein was quantitated by reading the absorbance at A280 and was stored at −20° C. in the presence of 50% glycerol. This preparation was used in in vitro DNA binding and DNA cleavage assays.

Example 9

Expression Screening for Soluble I-SceI and I-CreI Variants

I-SceI and I-CreI variants were cloned behind an N-terminal 6× His tag and TEV cleavage site into a vector containing an arabinose promoter and an araC repressor protein (Invitrogen). The plasmids were transformed into *E. coli* (Top10, Invitrogen) and plated on LB/carbenicillin (carb) agar. Single colonies were picked and used to inoculate 1 ml LB/carb cultures. The cultures were grown overnight at 37° C. with shaking to saturation. The overnight cultures were diluted about 1:30 into fresh LB/carb. Quadruplicate 3 ml cultures were set up and placed back into the 37° C. shaker and grown to mid-log phase (A600~0.6-0.8). Arabinose was added to 3 of the cultures to final concentrations of 0.2%, 0.02% and 0.002%. One culture was left without arabinose as an "non-induced" control. The cultures were incubated at 37° C. for an additional 3 hours. They were harvested by spinning at 3220×g for 10 minutes at 4° C. The media was decanted and the cell pellets stored at −20° C.

Cell pellets were thawed on ice and lysed by the addition of 250 ul Lysis Buffer (50 mM Sodium Phosphate, pH 7.0, 0.5 mg/ml lysozyme, Complete EDTA-free protease inhibitor cocktail (Roche)). The lysates were incubated on ice for 1 hour and then 50 ul of DNAseI cocktail (2.5M NaCl, 0.25 mg/ml MgCl2, 0.24 mg/ml DNAseI) was added to each. The lysates were incubated on ice for an additional hour and were spun for 2 minutes at 16000×g at 4° C. The supernatants containing the soluble proteins were placed into new tubes and 30 µl of a 50% slurry of Talon resin (Clontech) in Equilibration Buffer (50 mM Sodium Phosphate, pH 7.0, 500 mM NaCl, 5% glycerol) was added to each tube. The tubes were rocked for at least 1 hour at 4° C. The tubes were spun at 16000×g for 30 seconds at 4° C. to collect the resin and the supernatant was aspirated. The resin was washed 2× with 200 µl ice cold 1×PBS. The resins were resuspended in 30 µl 1×PBS and mixed with 4× Reducing Laemmli Buffer. The samples were heated at 99° C. for 5 minutes and loaded at 10 µl per lane onto 4-12% Tris-Bis gels (Invitrogen). The gels were run at 200 V for 30 minutes in MES Buffer (Invitrogen) and stained for total protein using Gel Code Blue (Pierce).

Highly expressed and soluble proteins were scaled up and purified to place into in vitro assays to assess DNA binding and cleavage activity.

Example 10

In vitro Binding and Cleavage Assay for I-CreI and I-SceI Variants

Preparation of DNA Substrate for Binding and Cleavage Assays

A DNA insert containing the I-SceI and I-CreI recognition sequences was prepared by annealing the following two oligonucleotides, followed by enzymatic phosphorylation:

```
                                                 SEQ ID NO: 46
5'-AATTCTGGTTCCGAAGCCTGTCCTGCACGCTAGGGATAACAGGGTAA

TAATATATGAATCCAAACTAGAGCGGGGCTCTTGACGTTTGGCTCAAAAC

GTCGTGAGACAGTTTGGTCAGTTGTAAATATCTAATATTCCAATG-3'

SEQ ID NO: 47
5'-GATCCATTGGAATATTAGATATTTACAACTGACCAAACTGTCTCACG

ACGTTTTGAGCCAAACGTCAAGAGCCCCGCTCTAGTTTGGATTCATATAT

TATTACCCTGTTATCCCTAGCGTGCAGGACAGGCTTCGGAACCAG-3'
```

The plasmid pUC 19 was digested with EcoRI and BamHI and the insert prepared as described above was ligated into the plasmid. The resulting plasmid, designated pSCI, was used to transform chemically-competent *E. coli*. Plasmid pSCI is propagated and purified using standard techniques.

The substrate for binding affinity assays was obtained from pSCI by digestion with EcoRI and BamHI and purification of the 142 base-pair fragment by agarose gel electrophoresis. DNA was quantified by absorbance at 260 nm.

The substrate for DNA cleavage assays was obtained from pSCI by digestion with AlwNI followed by enzymatic dephosphorylation and purification by agarose gel electrophoresis. DNA was quantified by absorbance at 260 nm.

Gel-Retardation Assay for Determination of Binding Affinities

Various concentrations of I-SceI or I-CreI (generally between 2.5 and 50 nM) were mixed with 5 nM DNA in 20 mM tris.HCl, 100 ug/mL bovine serum albumin, pH 8.0 (for I-SceI variants) or pH 9.0 (for I-CreI variants) in a total volume of 10 iL. After incubation for 20 minutes at 37° C., 1 iL of 10×DNA retardation gel loading buffer (Invitrogen) was added and the samples were loaded onto a 1 mm thick DNA retardation gel (Invitrogen). Electrophoresis was performed for 45 minutes at 175 Volts in 0.5× TBE buffer (Invitrogen). Gels were stained for 45 minutes with SYBR Gold stain (Invitrogen) and visualized by UV illumination. Densitometry was performed on a digital image of the gel to determine the relative intensities of the bands corresponding to bound and unbound DNA. Intensities of bound and unbound DNA were used to determine the concentrations of bound and free enzyme at each initial concentration. I-SceI variants (D44A, D145N) and I-CreI variant (D20N, Q47A) were shown to bind DNA. Binding affinities (dissociation constants, Kd) were determined by plotting the concentration of bound enzyme on the y-axis and the concentration of free enzyme on the x-axis for each data point and fitting the data to a rectangular hyperbola using standard nonlinear least-squares fitting procedures, using the equation y=([DNA]*x)/(Kd+x).

DNA Cleavage Assay

DNA cleavage of engineered endonucleases can be performed using the following assay. Approximately 250 ng of linearized pSCI was mixed with 90 to 250 ng of enzyme in a total volume of 20 iL in 10 mM tris.HCl, 10 mM MgCl2, 1 mM dithiothreitol, 100 ig/mL bovine serum albumin, pH 8.8. Samples were incubated for 1 hour at 37° C., loaded onto a 0.8% agarose E-gel (Invitrogen) and subjected to electrophoresis for 30 minutes. Bands were visualized by ultraviolet light. DNA cleavage was indicated by conversion of the 2807 base-pair substrate into two fragments of 1968 and 839 base-pairs (for I-CreI variants) or 1903 and 904 base-pairs (for I-SceI variants). Aspects of the cleavage assay may be altered for certain engineered endonucleases. For example, for I-CreI variants samples are heated for an additional 20 minutes at 70° C. For Sce-Fok fusions, a cleavage assay may be performed under the following conditions: 20 mM tris-HCl, 25 mM NaCl, 10 mM MgCl2, 100 ug/mL BSA, 5% glycerol, pH 9.0, 6 hrs at 42° C.

Example 11

In Vivo Assay for Active Engineered Meganuclease Library Screening

To distinguish active from inactive variants in a high throughput manner, an in vivo assay adapted from the selection system of Gruen et al. (Nucleic Acids Research, 2002, vol. 30, No. 7 e29: An in vivo Selection System for Homing Endonuclease Activity) is performed. Two plasmids are required: The first plasmid expresses Barnase, a lethal (to *E. coli*) RNAse. The Barnase open reading frame contains 2 amber stop mutations to ensure that no protein is not produced constitutively is placed under the additional control of an ara promoter and an araC repressor protein and is flanked by meganuclease recognition sites.

The engineered meganuclease library is be cloned in a separate plasmid behind a constitutive lac promoter. This plasmid also carries a supE tRNA cassette that allows read through of amber stop codons. When this plasmid is co-transformed with the Barnase containing plasmid into *E. coli*, the supE tRNA enables the production of the lethal Barnase in the presence of arabinose. The cells transformed with an active engineered meganuclease are producing an active meganuclease variant that can cut at the flanking recognition sequences. Cleavage of the Barnase gene and degradation of the linearized Barnase toxic gene is linked to cell survival cells. If the engineered meganuclease is inactive, the Barnase is produced and cell death occurs.

Cells that survive this assay contains rescuable plasmids containing active engineered meganucleases that may be produced in large scale and may be assayed in vitro for their DNA-binding activity and their DNA-cleavage activity as described in the above examples.

EQUIVALENTS

The present invention provides among other things methods for assembling large polynucleotide constructs and organisms having increased genomic stability. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein, including those items listed below, are hereby incorporated by reference in their entirety as if each individual publication or patent was specifically and individually indicated to be incorporated by reference. In case of conflict, the present application, including any definitions herein, will control.

The invention claimed is:

1. An engineered chimeric endonuclease comprising:
the nucleic acid binding domain of a nuclease deficient I-SceI linked to the nucleic acid cleavage domain of FokI,
wherein the nucleic acid binding domain of I-SceI endonuclease comprises an amino acid substitution at position 44 and 145, wherein the wild type residue aspartic acid (D) at position 44 is replaced with asparagine (N) or alanine (A) and wherein the wild type residue aspartic acid (D) at position 145 is replaced with alanine (A),
wherein the engineered chimeric endonuclease binds a recognition sequence motif recognized by I-SceI, and
wherein the engineered chimeric endonuclease cleaves at a unique cleavage position outside of the I-SceI recognition sequence motif.

2. The engineered chimeric endonuclease of claim 1, wherein the nucleic acid binding domain is a DNA binding domain.

3. The engineered chimeric endonuclease of claim 1, wherein the nucleic acid binding domain binds to a double-stranded recognition sequence motif.

4. The engineered chimeric endonuclease of claim 1, wherein the nucleic acid binding domain binds with nanomolar affinity to a target nucleic acid comprising the recognition sequence motif.

5. The engineered chimeric endonuclease of claim 1, wherein the nucleic acid binding domain is an inactive mutant catalytic domain of I-SceI.

6. The engineered chimeric endonuclease of claim 5, wherein the amino acid substitutions in the nucleic acid binding domain inactivate the catalytic endonuclease activity of I-SceI.

7. The engineered chimeric endonuclease of claim 1, wherein the cleavage domain comprises two identical FokI catalytic domains, two different FokI catalytic domains or a FokI catalytic domain and a catalytic domain from a different Type IIS endonuclease.

8. The engineered chimeric endonuclease of claim 7, wherein the cleavage domain comprises a catalytic domain from a BstF5 I, BtsC I, BsrD I, Bts I, Alw I, Bcc I, BsmA I, Ear I, Mly I, Ple I, Bmr I, Bsa I, BsmB I, Fau I, Mnl I, Sap I, Bbs I, BciV I, Hph I, Mbo II, BfuA I, BspCN I, BspM I, SfaN I, Hga I, BseR I, Bbv I, Eci I, BceA I, BsmF I, BtgZ I, BpuE I, Bsg I, Mme I, BseG I, Bse3D I, BseM I, AclW I, Alw26 I, Bst6 I, BstMA I, Eam1104 I, Ksp632 I, Pps I, Sch I, Bfi I, Bso31 I, BspTN I, Eco31 I, Esp3 I, Smu I, Bfu I, Bpi I, BpuA I, BstV2 I, AsuHP I, Acc36 I, Lwe I, Aar I, BseM II, TspDT I, TspGW I, BseX I, BstV1 I, Eco57 I, Eco57M I, Gsu I, or a Bcg I Type IIS endonuclease.

9. The engineered chimeric endonuclease of claim 1, wherein the cleavage domain comprises at least one catalytic domain of a Fok I restriction endonuclease.

10. The engineered chimeric endonuclease of claim 9, wherein the cleavage domain comprises the at least one catalytic domain of a FokI restriction endonuclease associated with at least one portion of a DNA recognition subdomain of the FokI restriction endonuclease.

11. The engineered chimeric endonuclease of claim 1, wherein the nucleic acid binding domain and the nucleic acid cleavage domain are covalently linked without an intervening synthetic peptide linker.

12. The engineered chimeric endonuclease of claim 1, wherein the nucleic acid binding domain and the nucleic acid cleavage domain are linked via an intervening synthetic peptide linker.

* * * * *